(12) United States Patent
Chung et al.

(10) Patent No.: US 10,925,923 B2
(45) Date of Patent: Feb. 23, 2021

(54) PEPTIDE HAVING ANTI-INFLAMMATORY ACTIVITY, AND USE THEREOF

(71) Applicant: CAREGEN CO., LTD., Anyang-si (KR)

(72) Inventors: Yong Ji Chung, Yongin-si (KR); Eun Mi Kim, Yongin-si (KR)

(73) Assignee: CAREGEN CO., LTD., Anyang-Si (KR)

( * ) Notice: Subject to any disclaimer, the term of this patent is extended or adjusted under 35 U.S.C. 154(b) by 0 days.

(21) Appl. No.: 16/091,779

(22) PCT Filed: Mar. 29, 2017

(86) PCT No.: PCT/KR2017/003446
§ 371 (c)(1),
(2) Date: Oct. 5, 2018

(87) PCT Pub. No.: WO2017/179838
PCT Pub. Date: Oct. 19, 2017

(65) Prior Publication Data
US 2019/0091278 A1 Mar. 28, 2019

(30) Foreign Application Priority Data
Apr. 15, 2016 (KR) .......... 10-2016-0046089

(51) Int. Cl.
| A61K 38/07 | (2006.01) |
| A61K 38/08 | (2019.01) |
| C07K 5/10 | (2006.01) |
| C07K 7/06 | (2006.01) |
| A61P 29/00 | (2006.01) |

(52) U.S. Cl.
CPC .......... *A61K 38/07* (2013.01); *A61K 38/08* (2013.01); *A61P 29/00* (2018.01); *C07K 5/10* (2013.01); *C07K 7/06* (2013.01); *Y02A 50/30* (2018.01)

(58) Field of Classification Search
None
See application file for complete search history.

(56) References Cited

U.S. PATENT DOCUMENTS

| 2007/0044171 A1* | 2/2007 | Kovalic ............... A01G 22/00 800/278 |
| 2009/0175821 A1* | 7/2009 | Bridon ............... A61K 38/38 424/85.5 |
| 2014/0357512 A1* | 12/2014 | Yang ............... G01N 33/57407 506/9 |
| 2015/0125438 A1 | 5/2015 | Kim et al. |
| 2017/0049847 A1 | 2/2017 | Chung et al. |

FOREIGN PATENT DOCUMENTS

| KR | 10-2014-0135403 A | 11/2014 |
| KR | 10-2015-0031413 A | 3/2015 |
| KR | 10-2015-0130616 A | 11/2015 |
| KR | 10-2015-0130617 A | 11/2015 |
| KR | 10-2016-0003610 A | 1/2016 |
| WO | WO-2008/142517 A2 | 11/2008 |
| WO | WO-2014/102009 A1 | 7/2014 |

OTHER PUBLICATIONS

Search results for NCBI Blast Protein Sequence Search for SEQ ID No. 1 conducted Nov. 6, 2019 (Year: 2019).*
Search results for NCBI Blast Protein Sequence Search for SEQ ID No. 2 conducted Nov. 6, 2019 (Year: 2019).*
Search results for NCBI Blast Protein Sequence Search for SEQ ID No. 3 conducted Nov. 6, 2019 (Year: 2019).*
International Search Report dated Aug. 1, 2017 for International Patent Application No. PCT/KR2017/003446, Chung et al., "Peptide Having Anti-Inflammatory Activity, and Use Thereof," filed Mar. 29, 2017 (8 pages).

* cited by examiner

*Primary Examiner* — Christina Bradley
(74) *Attorney, Agent, or Firm* — Clark & Elbing LLP; Susan M. Michaud

(57) ABSTRACT

The present invention provides a peptide having anti-inflammatory activity, composed of an amino acid sequence of a sequence listing of SEQ ID NO: 1, SEQ ID NO: 2 or SEQ ID NO: 3. The peptide inhibits the expression of inflammatory cytokines and inhibits the proliferation of inflammatory cells, so as to resultantly exhibit anti-inflammatory activity, thereby being useful in the prevention or treatment of inflammatory diseases.

20 Claims, 32 Drawing Sheets

Specification includes a Sequence Listing.

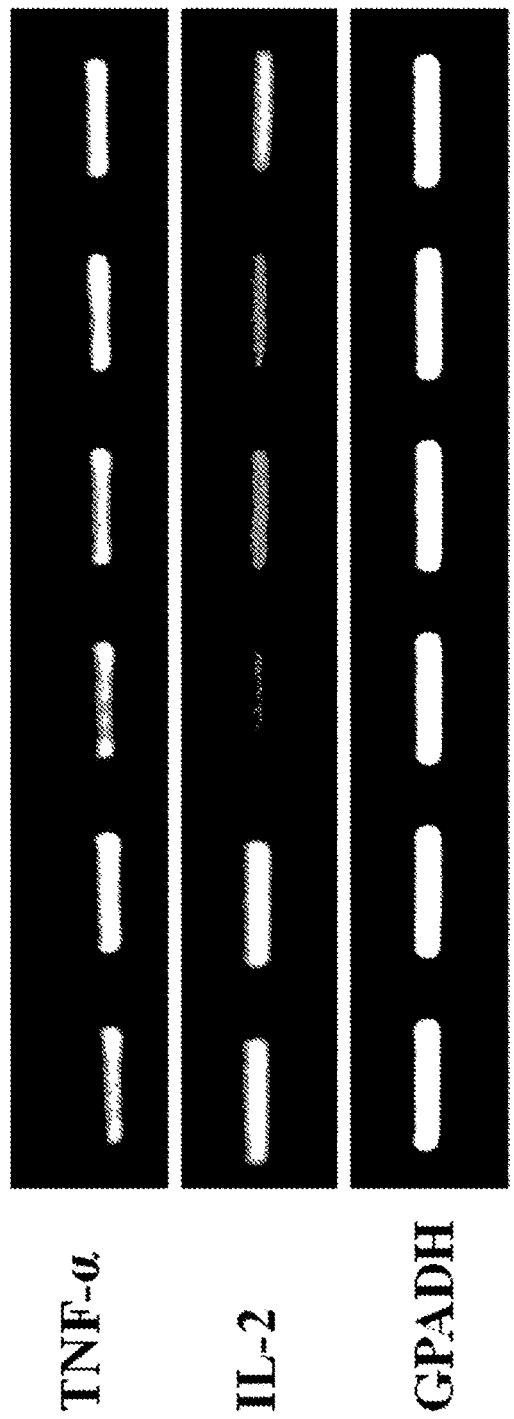

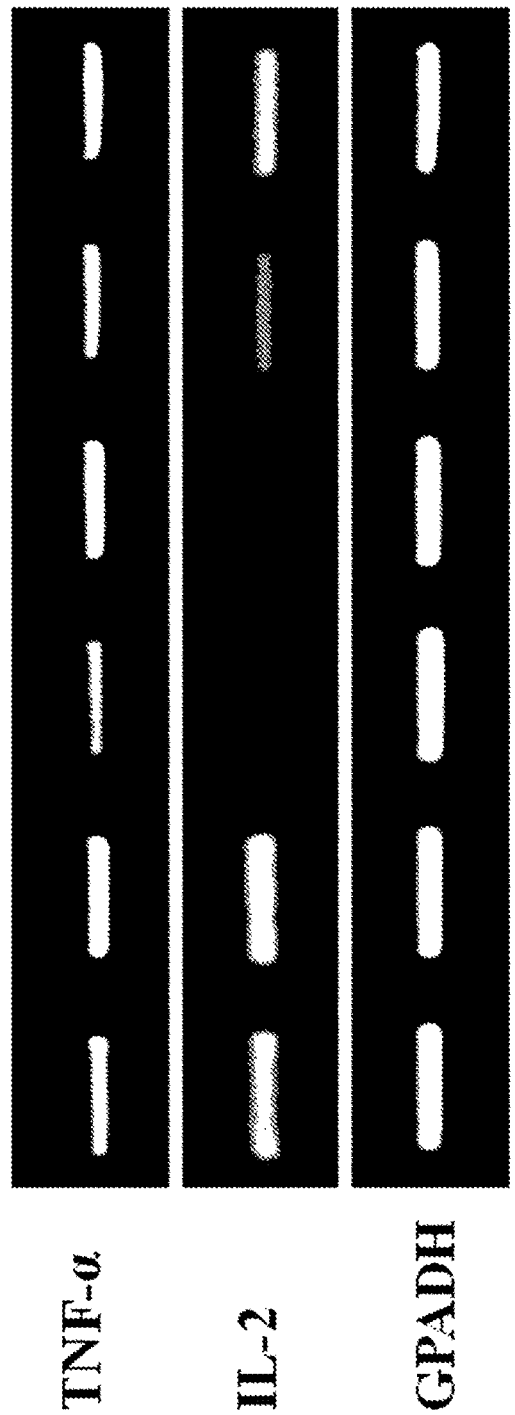

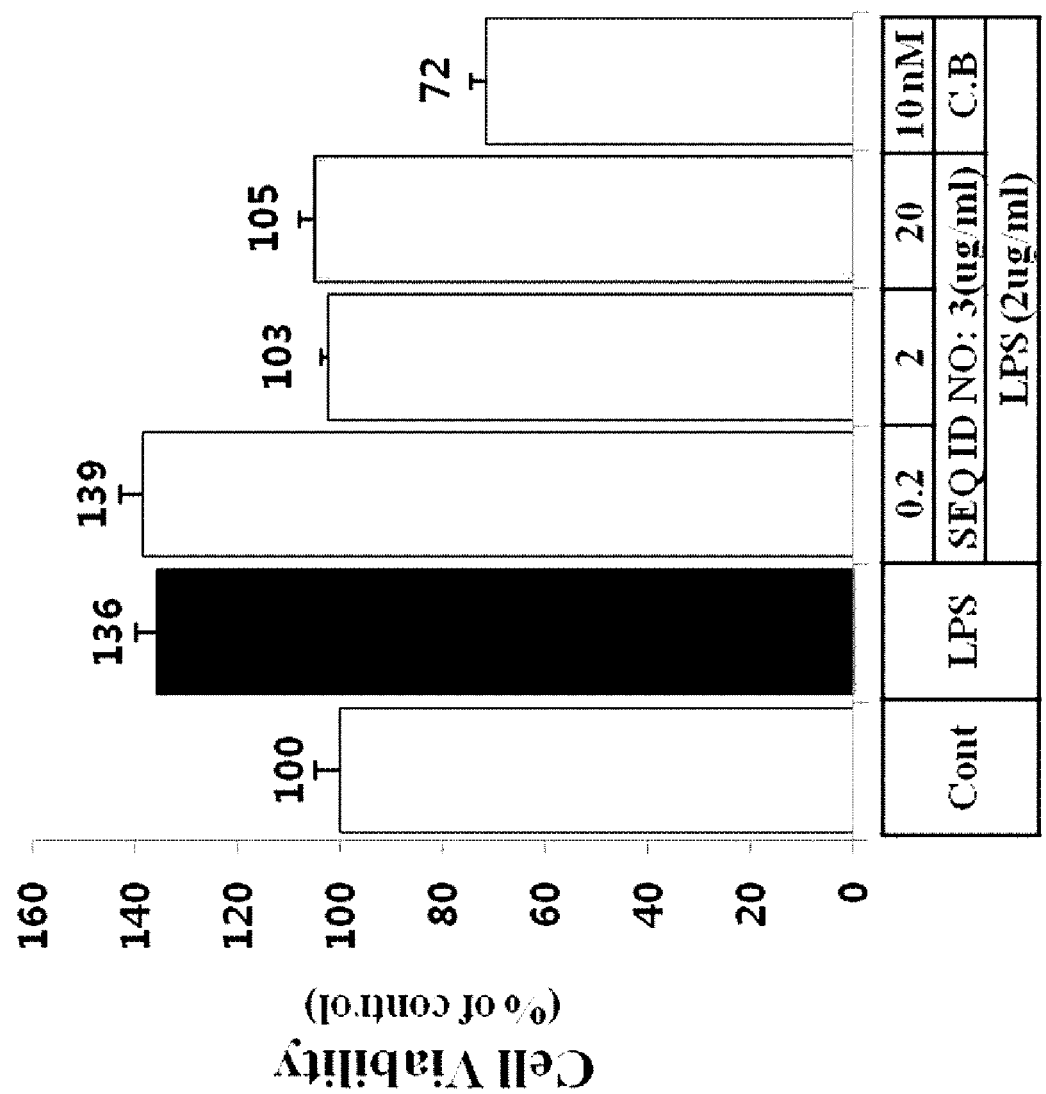

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Thr Met Arg Asp
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Asp Asn Cys Leu Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Gly Val Gln His Gln Ala Ser Pro Tyr
1               5

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
cgtcagccga ttrtgctatc t                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
cggactccgc aaagtctaag                                                20

<210> SEQ ID NO 6
<211> LENGTH: 20
<212> TYPE: DNA
<213> ORGANISM: Artificial Sequence
```

```
<220> FEATURE:
<223> OTHER INFORMATION: Synthetic Construct

<400> SEQUENCE: 6
ctcgcttcct gtgtcacatt                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
atcctgggga gtttcaggtt                                               20
```

PEPTIDE HAVING ANTI-INFLAMMATORY ACTIVITY, AND USE THEREOF

TECHNICAL FIELD

The present invention relates to a peptide having anti-inflammatory activity and a use thereof.

BACKGROUND ART

Inflammatory responses are a series of composite physiological responses, such as enzyme activation, inflammatory mediator secretion, body fluid infiltration, cell migration, and tissue destruction, and external symptoms, such as erythema, edema, fever, and pain, which occur in association with various inflammatory mediators and immune cells in topical blood vessels and body fluids, when tissues or cells are damaged or infected with external infection sources (e.g., bacteria, fungi, viruses, various kinds of allergens).

Specifically, when foreign bacteria invade into a specific tissue and proliferate, the leukocytes in the living body recognize such a condition and attack actively the proliferating foreign bacteria. The dead leukocytes generated during the process are accumulated in the tissue invaded by the bacteria while the cell debris of the invading bacteria killed by leukocytes is lysed in the tissue, resulting in formation of abscesses.

In the case of a normal, inflammatory responses act to remove foreign infection sources and regenerate damaged tissue to restore functions of living organisms. However, when antigens are not removed or inflammatory responses occur excessively or continuously due to intrinsic substances, such inflammatory responses cause acute inflammation as life-threatening diseases, joint diseases such as rheumatoid arthritis, skin diseases such as psoriasis or the like, and allergic inflammatory diseases, such as bronchial asthma, and also act as obstacles in treatment processes, such as blood transfusion, drug administration, and organ transplantation.

Tumor necrosis factor-α (TNF-α) is a cytokine that is produced by macrophages and various several cells, which are activated in host immune responses for bacterial infection and tumor diseases. This cytokine has also been known as an important medium in the inflammatory responses, and is an inflammatory cytokine that plays a key role in inflammatory diseases, such as rheumatoid arthritis (RA), psoriatic arthritis, Crohn's disease, psoriasis, and ankylosing spondylitis (AS).

For example, TNF-α keeps synovial inflammation and continuously destroys bones and cartilage in rheumatoid arthritis. Therefore, the inhibition of the specific biological activity of TNF-α is required, and thus various biological preparations for inhibiting TNF-α have been developed for the purpose of preventing the cellular response mediated by TNF-α and adjusting activities of pro-inflammatory cytokines and the procedures regulated by TNF-α.

There are dexamethasone and cortisone using adrenocortical hormone components, as current inflammation medicines. However, these act as inflammation medicines, but have strong toxicity and often cause symptoms such as edema, as side effects thereof.

In some cases, these medicines may not act selectively on the causes of inflammation, causing severe immune suppression [Check W. A. and Kaliner M. A., Am. Rev. Respir. Dis., 141, p 44-51. 1990].

Steroid drugs using adrenocortical hormones, which are currently available anti-inflammatory agents, also show severe side effects, such as edema, and, therefore, it is urgent to develop non-steroidal medicines with no side effects.

DETAILED DESCRIPTION OF THE INVENTION

Technical Problem

The present inventors endeavored to develop excellent peptides having biologically effective activity. As a result, the present inventors established that a peptide composed of one amino acid sequence selected from the group consisting of amino acid sequences of SEQ ID NO: 1, SEQ ID NO: 2 and SEQ ID NO: 3 has anti-inflammatory activity, and thus completed the present invention.

Accordingly, an aspect of the present invention is to provide a peptide having anti-inflammatory activity.

Another aspect of the present invention is to provide an anti-inflammatory composition.

Technical Solution

In accordance with an aspect of the present invention, there is provided a peptide having anti-inflammatory activity consisting of an amino acid sequence of SEQ ID NO: 1, SEQ ID NO: 2 or SEQ ID NO: 3.

The present inventors endeavored to develop excellent peptides having biologically effective activity. As a result, the present inventors established that a peptide consisting of an amino acid sequence of SEQ ID NO: 1, SEQ ID NO: 2 or SEQ ID NO: 3 has anti-inflammatory activity.

The peptide of the present invention may include an amino acid sequence of SEQ ID NO: 1, SEQ ID NO: 2 or SEQ ID NO: 3, and may be composed of an amino acid sequence of SEQ ID NO: 1, SEQ ID NO: 2 or SEQ ID NO: 3.

The bacterial endotoxin, lipopolysaccharide (LPS), stimulates the production of inflammation factors, such as iNOS, COX-2, TNF-α, intracellular ROS, and various interleukins in macrophages (Hinz, B., Brune, K. Cyclooxygenase-2-10 years later. J Pharmacol Exp Ther 300(2):367-375, 2002; and Anti-oxidative and anti-inflammatory effect of fractionated extracts of *Draconis* Resina in macrophages, The Korean Journal of Herbology, 23(2):179-192, 2008.) It is therefore considered that substances to inhibit inflammation factors produced by LPS can be favorably used in the treatment of various inflammatory diseases involved in activity of macrophages.

According to the present invention, the peptide consisting of an amino acid sequence of SEQ ID NO: 1, SEQ ID NO: 2 or SEQ ID NO: 3 inhibits the expression of inflammatory cytokines, inhibits the expression of the inflammation-related factor COX-2, reduces the production of ROS, and suppresses the activation of T cells, thereby ultimately suppressing inflammation responses.

According to an embodiment of the present invention, the peptide consisting of an amino acid sequence of SEQ ID NO: 1, SEQ ID NO: 2 or SEQ ID NO: 3 of the present invention inhibits the expression of the inflammatory cytokines TNF-α, IL-2, IFN-γ, IL-1β, IL-6, IL-15, IL-18, GM-CSF, and IFN-α. More preferably, the peptide of the present invention inhibits the expression of TNF-α, IL-2, and IFN-γ.

According to another embodiment of the present invention, the peptide of the present invention inhibits the expression of COX-2, which is an enzyme playing an important role in the regulation of inflammation responses, by stimulating the biosynthesis of prostaglandins. COX-2 is rarely expressed in normal conditions, but rapidly expressed by mitogenic stimulations, such as inflammation factors or cytokines, endotoxins, or oncogenic genes.

According to another embodiment of the present invention, the peptide of the present invention reduces the production of reactive oxygen species (ROS), which is an important factor in the inflammatory responses. Mitochondria and enzymes, such as peroxisome, xanthine oxidase (XOD), NADPH oxidase, and COX, which are present in cells, continuously produce ROS, and reactive nitrogen species (RNS) is produced in large quantities due to the immune responses of macrophages, neutrophils, and other immune cells at the time of immune responses, and here ROS are also produced (Delanty, N., Dichter, M. A. Oxidative injury in the nervous system. ActaNeurolScand 98: 145-153, 1998: and Brune, B., Zhou, J., Von Knethen, A. Nitric oxide, oxidative stress, and apoptosis. Kidney Int Suppl 84: 22-24, 2003).

Inflammatory responses correspond to a series of activation mechanisms to enhance the in vivo restoration systems and reduce the damage thereof, and the inflammatory responses are regulated by very complicated mechanisms. It is important that the inflammatory responses sustained by repeated tissue damage or regeneration produce large quantities of ROS and RNS in inflammation-related cells, resulting in permanent gene degeneration, causing pathological conditions (Kaplanski, G., et al., IL-6: a regulator of the transition from neutrophil to monocyte recruitment during inflammation. Trends Immunol 24(1):25-29, 2003.). As such, ROS and RNS are very closely related to inflammatory responses.

According to another embodiment of the present invention, the peptide of the present invention suppresses the activation of T cells. The peptide of the present invention inhibits the expression of CD3 and CD25, which are T-cell activation expression markers, in cells in which inflammation responses are induced by LPS.

According to another embodiment of the present invention, the peptide of the present invention suppresses the proliferation of inflammatory cells.

As used herein, the term "peptide" refers to a linear molecule formed by amino acid residues linked to each other via peptide linkages. The peptide of the present invention may be prepared by known chemical synthesis methods, especially, solid-phase synthesis techniques (solid-phase synthesis techniques; Merrifield, *J. Amer. Chem. Soc.* 85:2149-54(1963); and Stewart, et al., *Solid Phase Peptide Synthesis,* 2nd. ed., Pierce Chem. Co.: Rockford, 111(1984)) or liquid-phase synthesis techniques (U.S. Pat. No. 5,516,891).

According to an embodiment of the present invention, a protecting group, which is selected from the group consisting of an acetyl group, a fluorenyl methoxy carbonyl group, a formyl group, a palmitoyl group, a myristyl group, a stearyl group, and polyethylene glycol (PEG), may be linked to the N- or C-terminus of the peptide.

The foregoing amino acid modification functions to significantly improve the stability of the peptide of the present invention. As used herein, the term "stability" refers to storage stability (e.g., room-temperature storage stability) as well as in vivo stability. The foregoing protective group acts to protect the peptide of the present invention from the attack by protein cleavage enzymes in vivo.

In accordance with another aspect of the present invention, there is provided an anti-inflammatory composition containing, as an active ingredient, at least one peptide selected from the group consisting of peptides consisting of an amino acid sequence of SEQ ID NO: 1, SEQ ID NO: 2 and SEQ ID NO: 3.

Since the anti-inflammatory composition contains, as an active ingredient, the foregoing peptide consisting of an amino acid sequence of SEQ ID NO: 1, SEQ ID NO: 2 or SEQ ID NO: 3, the descriptions of overlapping contents therebetween are omitted to avoid excessive complexity of the present specification.

The peptide consisting of an amino acid sequence of SEQ ID NO: 1, SEQ ID NO: 2 or SEQ ID NO: 3 is very effective in the prevention or treatment of inflammatory diseases by inhibiting the expression of inflammatory cytokines and suppressing the proliferation of inflammatory cells.

The inflammatory disease, to which the anti-inflammatory composition of the present invention can be applied, includes atopic dermatitis, encephalitis, inflammatory enteritis, chronic obstructive pulmonary disease, pulmonary hemorrhagic shock, pulmonary fibrosis, undifferentiated spondyloarthropathy, undifferentiated arthropathy, arthritis, inflammatory osteolysis, chronic inflammation diseases by chronic viral or bacterial infections, colitis, inflammatory enteropathy, type 1 diabetes, rheumatoid arthritis, reactive arthritis, osteoarthritis, psoriasis, scleroderma, osteoporosis, atherosclerosis, myocarditis, endocarditis, pericarditis, cystic fibrosis, Hashimoto's thyroiditis, Graves' disease, leprosy, syphilis, Lyme disease, borreliosis, neurogenic borreliosis, tuberculosis, sarcoidosis, lupus, discoid lupus, chilblain lupus, lupus nephritis, systemic lupus erythematosus, macular degeneration, uveitis, irritable bowel syndrome, Crohn's disease, Sjogren's syndrome, fibromyalgia, chronic fatigue syndrome, chronic fatigue and immune dysfunction syndrome, myalgic encephalomyelitis, amyotrophic lateral sclerosis, Parkinson's disease, and multiple sclerosis, but is not limited thereto.

The composition for prevention or treatment of the inflammatory disease may be prepared into a pharmaceutical composition.

When the composition of the present invention is prepared into a pharmaceutical composition, the composition of the present invention may contain: (a) a pharmaceutically effective amount of the foregoing peptide of the present invention; and (b) a pharmaceutically acceptable carrier, but is not limited thereto.

As used herein, the term "pharmaceutically effective amount" refers to an amount sufficient to attain the efficacy or activity of the foregoing peptide.

The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and/or mineral oil.

The pharmaceutical composition of the present invention may further contain a lubricant, a wetting agent, a sweetening agent, a flavoring agent, an emulsifier, a suspending agent, a preservative, and the like, in addition to the above ingredients.

Suitable pharmaceutically acceptable carriers and agents are described in detail in *Remington's Pharmaceutical Sciences* (19th ed., 1995).

The pharmaceutical composition of the present invention may be administered orally or parenterally, preferably parenterally, and examples of the parenteral administration may include intravenous injection, subcutaneous injection, intramuscular injection, intraperitoneal injection, topical administration, and transdermal administration.

A suitable dose of the pharmaceutical composition of the present invention may vary depending on various factors, such as the method for formulation, the manner of administration, the age, body weight, gender, and morbidity of the patient, diet, the time of administration, the excretion rate, and response sensitivity. Meanwhile, the dose of the pharmaceutical composition of the present invention is 0.0001-200 µg per day.

The pharmaceutical composition of the present invention may be formulated into a unit dosage form or a multi-dose container using a pharmaceutically acceptable carrier and/or excipient according to the method easily conducted by a person having ordinary skills in the art to which the present invention pertains.

Here, the dosage form may be a solution in an oily or aqueous medium, a suspension, an emulsion, an extract, a powder, granules, a tablet, a capsule, or a gel (e.g., a hydrogel), and may further include a dispersant or a stabilizer.

Advantageous Effects

The present invention is directed to a peptide having anti-inflammatory activity and consisting of an amino acid sequence of SEQ ID NO: 1, SEQ ID NO: 2 or SEQ ID NO: 3. The peptide inhibits the expression of inflammatory cytokines and suppresses the proliferation of inflammatory cells, ultimately showing anti-inflammatory activity, and thus can be favorably used in the prevention or treatment of inflammatory diseases.

BRIEF DESCRIPTION OF THE DRAWINGS

FIG. 1a shows the RT-PCR results confirming the expression changes of TNF-α and IL-2 by a peptide composed of the amino acid sequences of SEQ ID NO: 1 according to an embodiment of the present invention.

FIG. 1d shows the RT-PCR results confirming the expression changes of TNF-α and IL-2 by a peptide composed of the amino acid sequences of SEQ ID NO: 2 according to an embodiment of the present invention.

FIG. 4f shows the proliferation assay results by a peptide composed of the amino acid sequence of SEQ ID NO: 3 according to an embodiment of the present invention.

BEST MODE FOR CARRYING OUT THE INVENTION

Figure 1B:
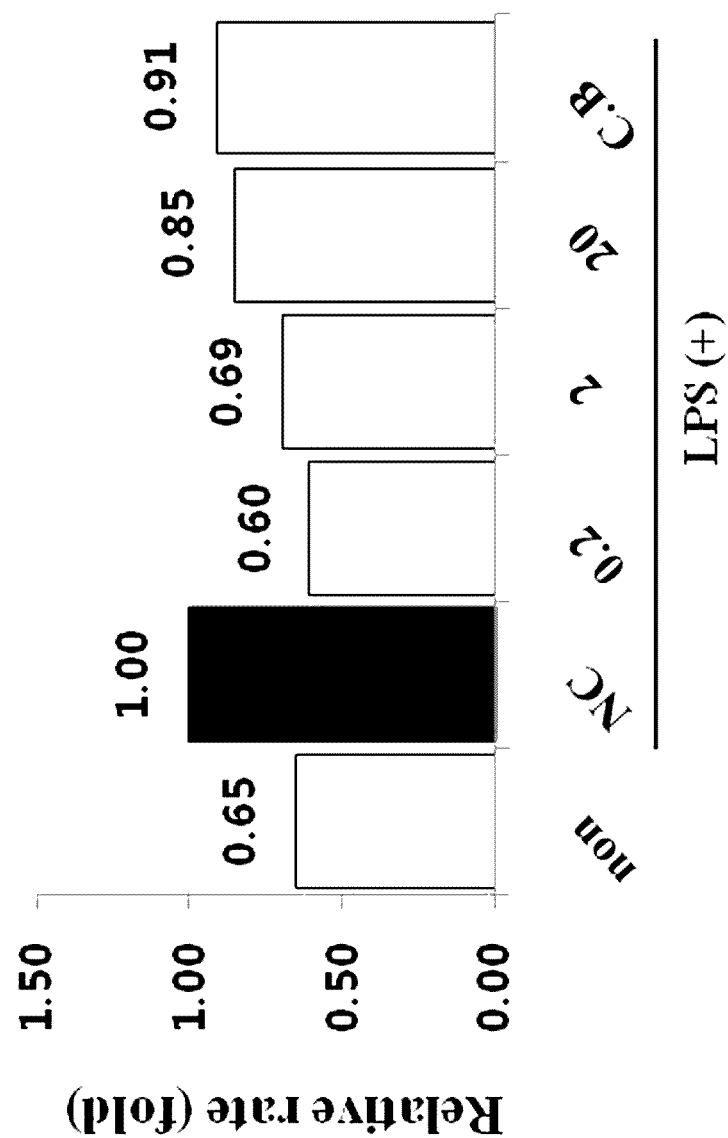
FIG. 1b is a graph of the RT-PCR results confirming the expression change of TNF-α by a peptide composed of the amino acid sequences of SEQ ID NO: 1 according to an embodiment of the present invention.
Figure 1C:
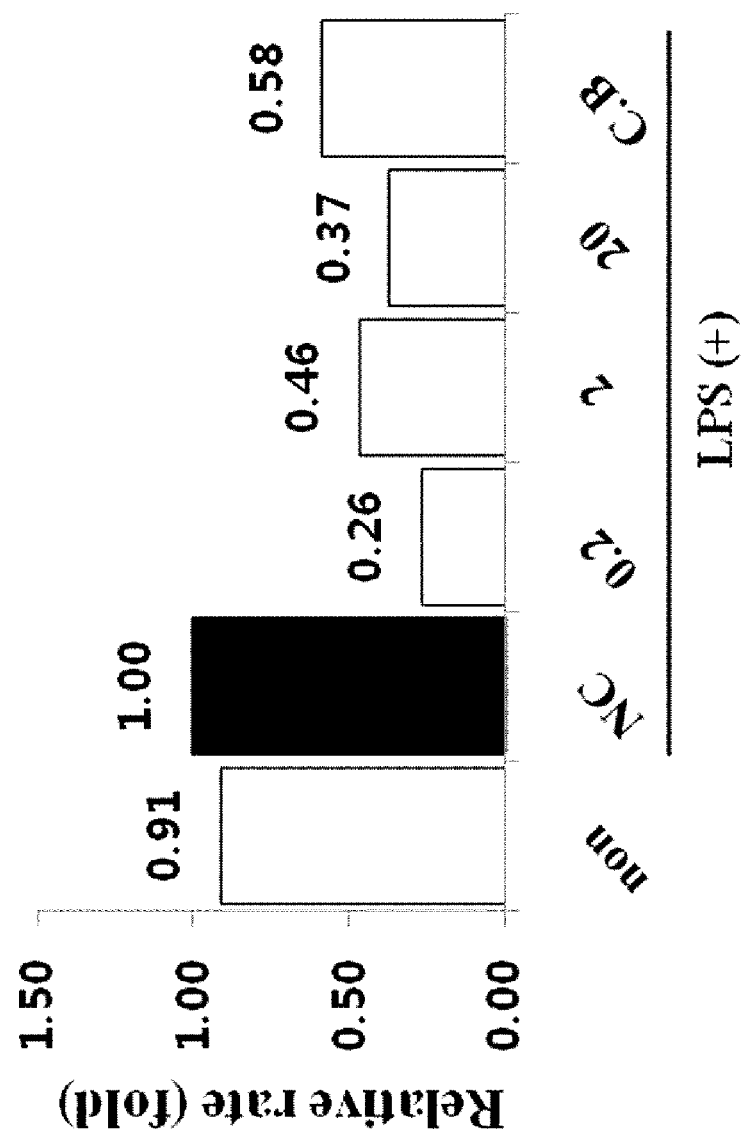
FIG. 1c is a graph of the RT-PCR results confirming the expression change of IL-2 by a peptide composed of the amino acid sequences of SEQ ID NO: 1 according to an embodiment of the present invention.
Figure 1E:
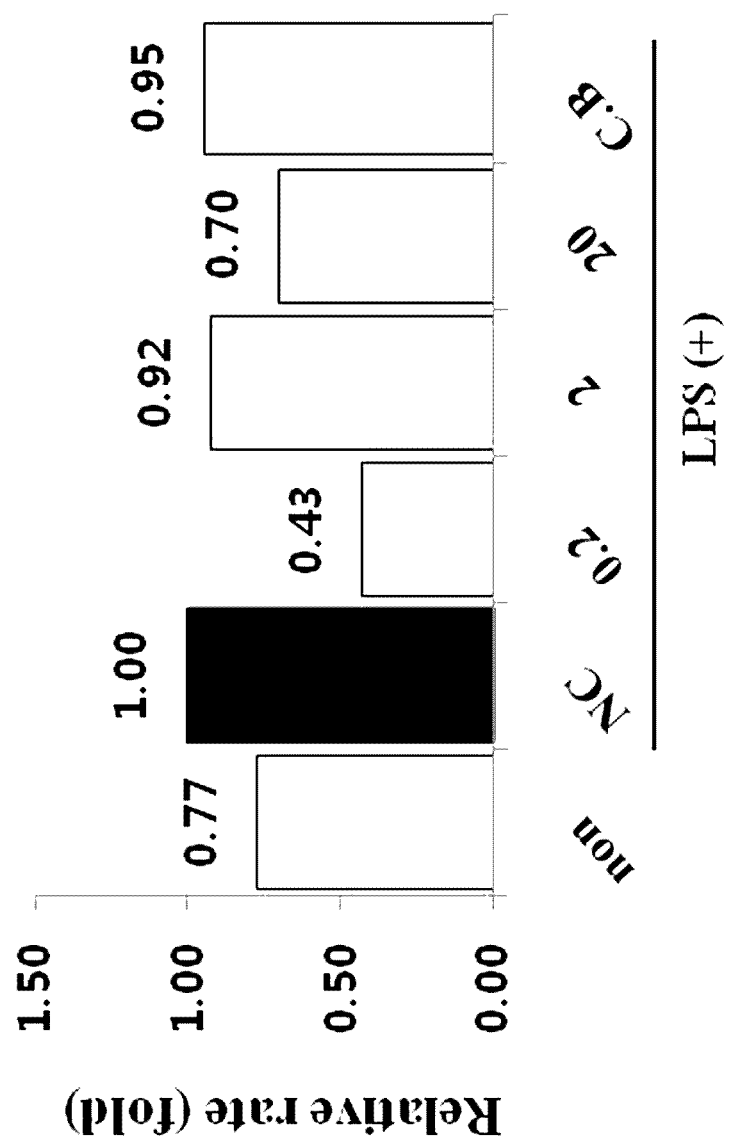
FIG. 1e is a graph of the RT-PCR results confirming the expression change of TNF-α by a peptide composed of the amino acid sequences of SEQ ID NO: 2 according to an embodiment of the present invention.
Figure 1F:
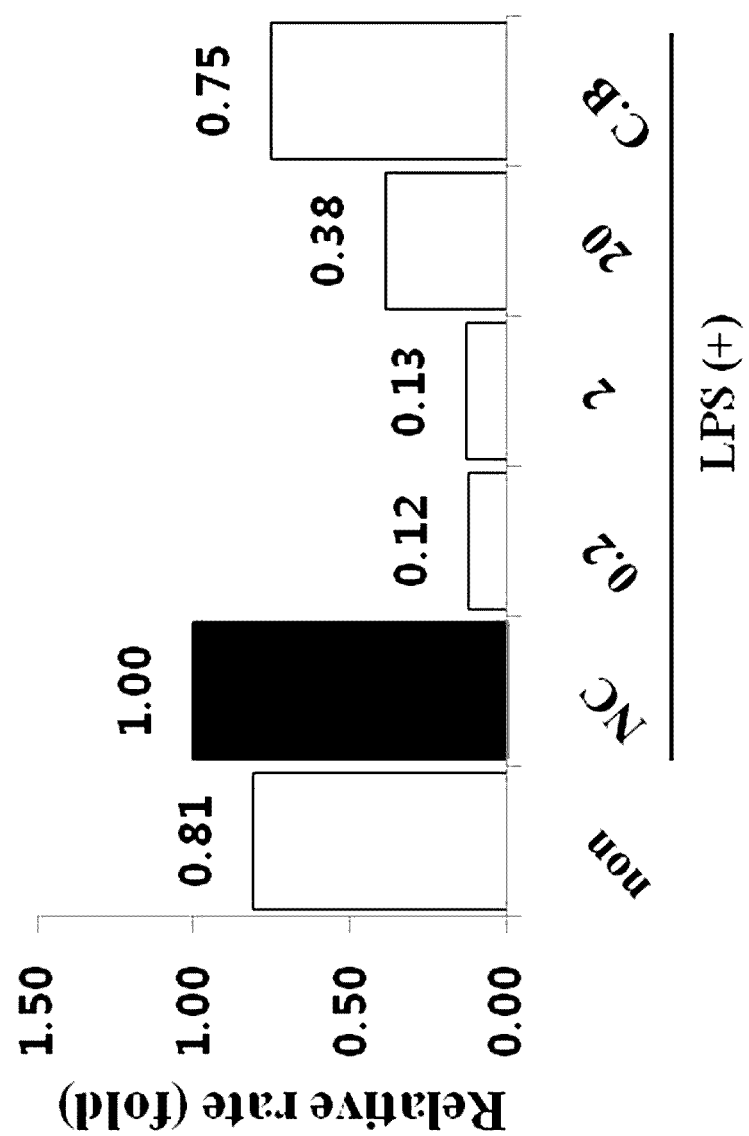
FIG. 1f is a graph of the RT-PCR results confirming the expression change of IL-2 by a peptide composed of the amino acid sequences of SEQ ID NO: 2 according to an embodiment of the present invention.
Figure 1G:
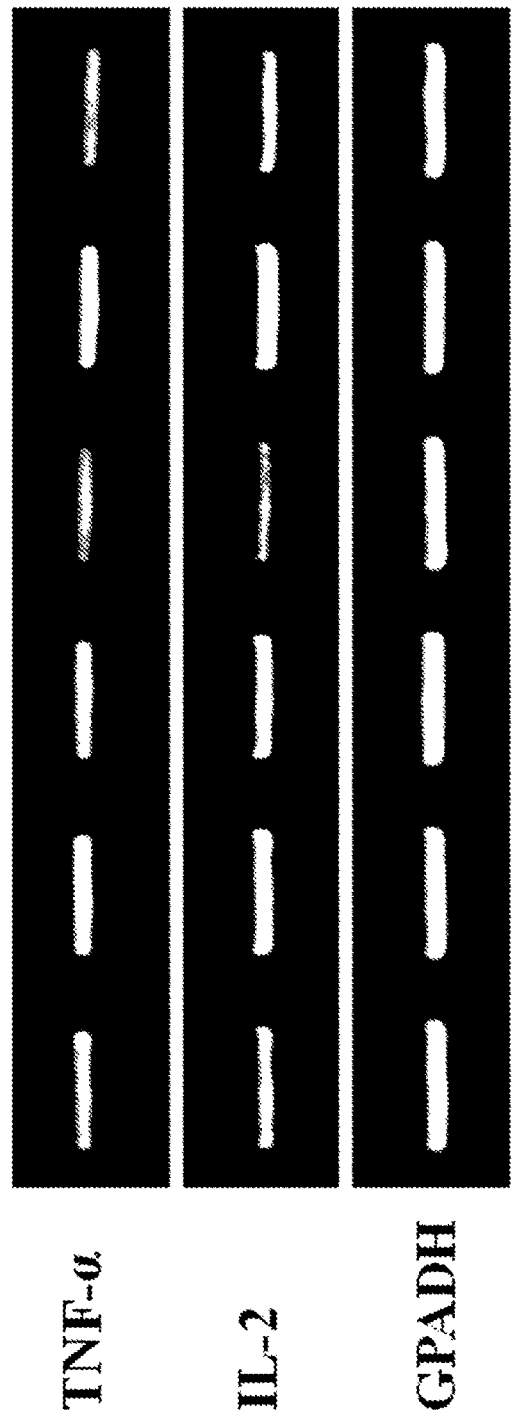
FIG. 1g shows the RT-PCR results confirming the expression changes of TNF-α and IL-2 by a peptide composed of the amino acid sequences of SEQ ID NO: 3 according to an embodiment of the present invention.
Figure 1H:
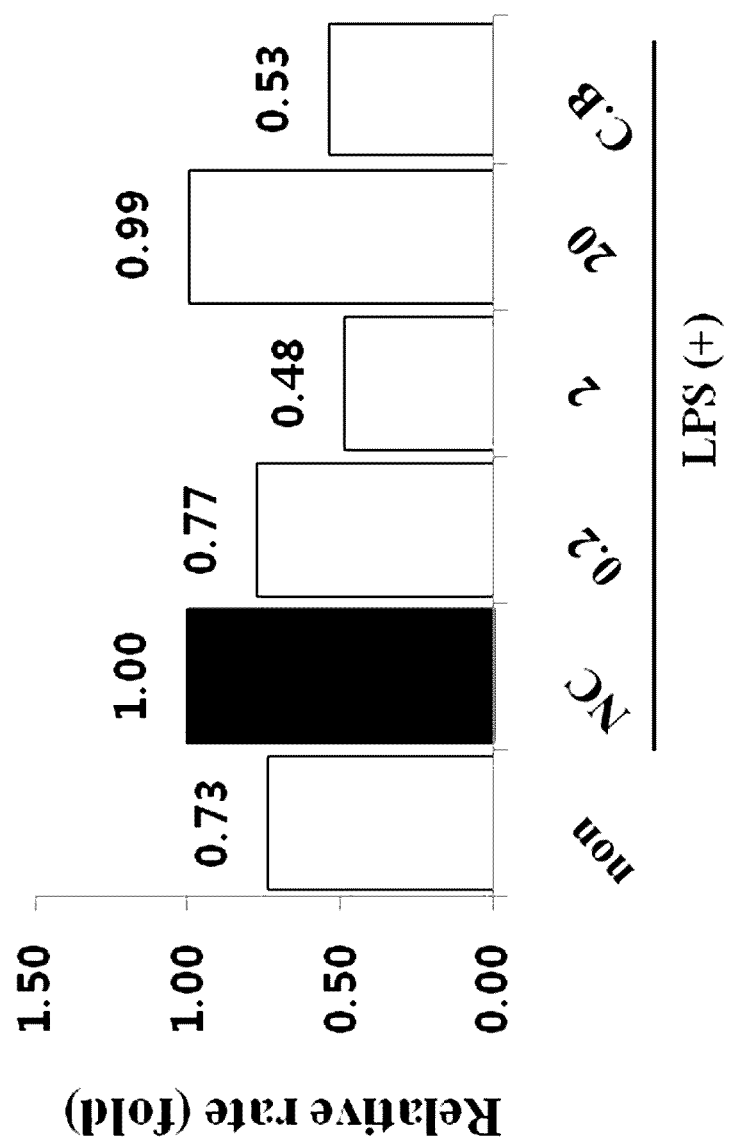
FIG. 1h is a graph of the RT-PCR results confirming the expression change of TNF-α by a peptide composed of the amino acid sequences of SEQ ID NO: 3 according to an embodiment of the present invention.
Figure 1I:
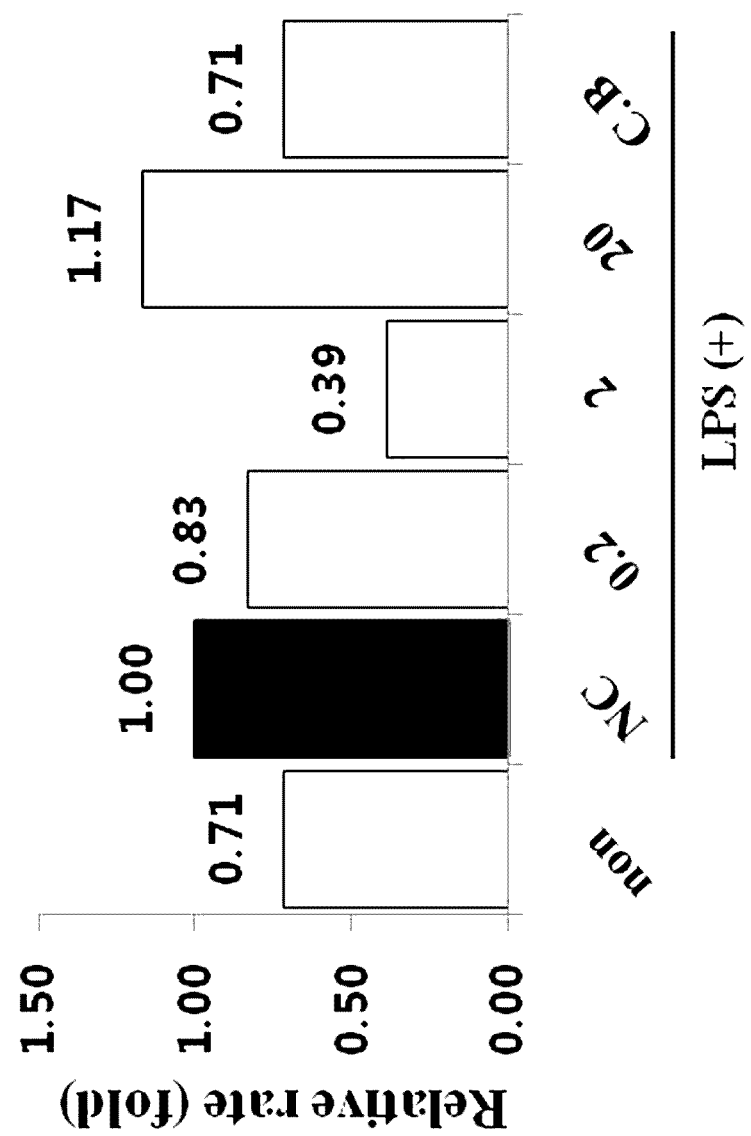
FIG. 1i is a graph of the RT-PCR results confirming the expression change of IL-2 by a peptide composed of the amino acid sequences of SEQ ID NO: 3 according to an embodiment of the present invention.
Figure 2A:
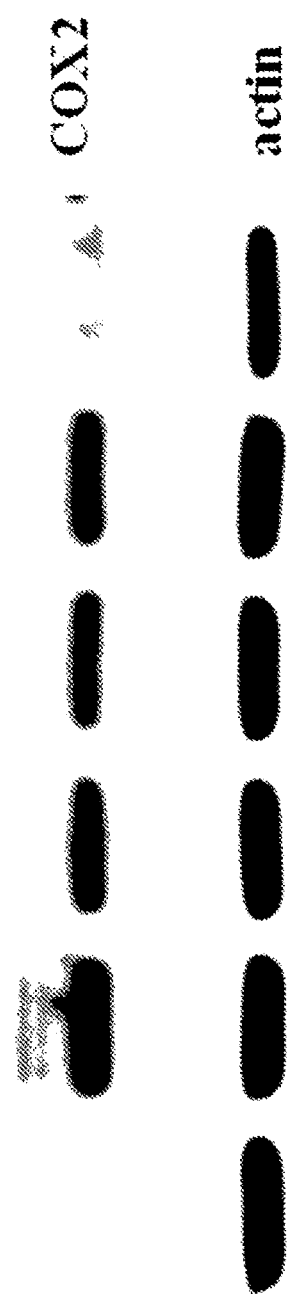
FIG. 2a shows the western blot results confirming the expression change of COX2 by a peptide composed of the amino acid sequence of SEQ ID NO: 1 according to an embodiment of the present invention.
Figure 2B:
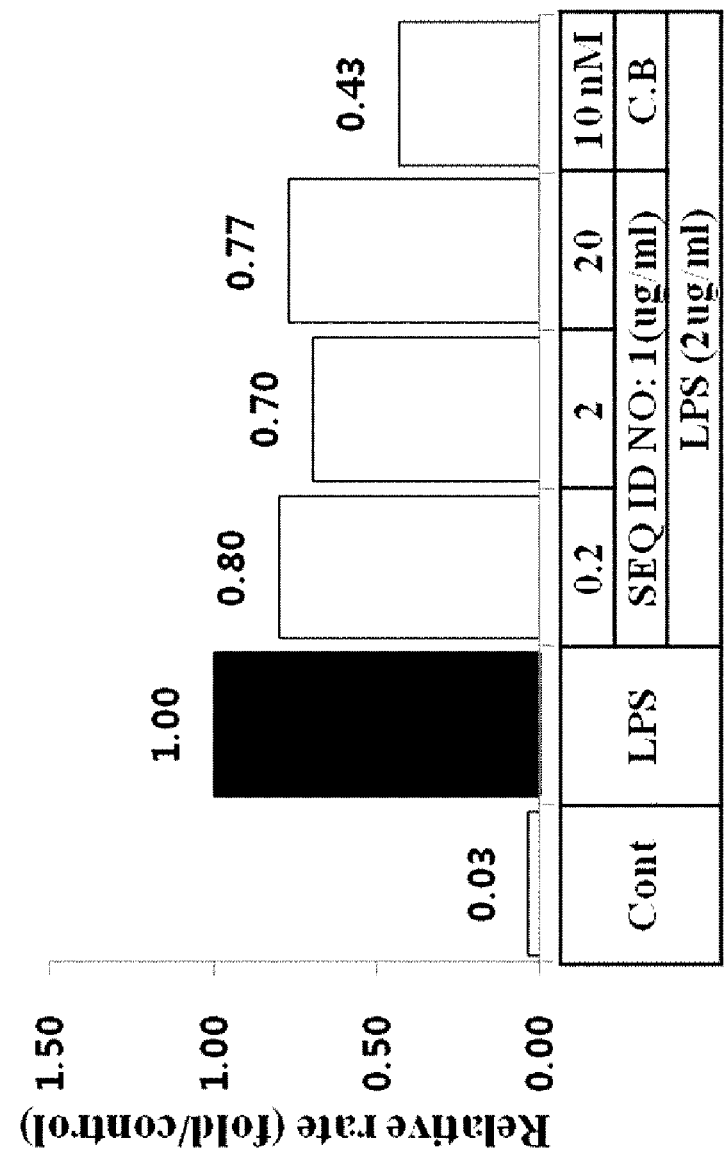
FIG. 2b is a graph of the western blot results confirming the expression change of COX2 by a peptide composed of the amino acid sequence of SEQ ID NO: 1 according to an embodiment of the present invention.
Figure 2C:
FIG. 2c shows the western blot results confirming the expression change of COX2 by a peptide composed of the amino acid sequence of SEQ ID NO: 2 according to an embodiment of the present invention.
Figure 2D:
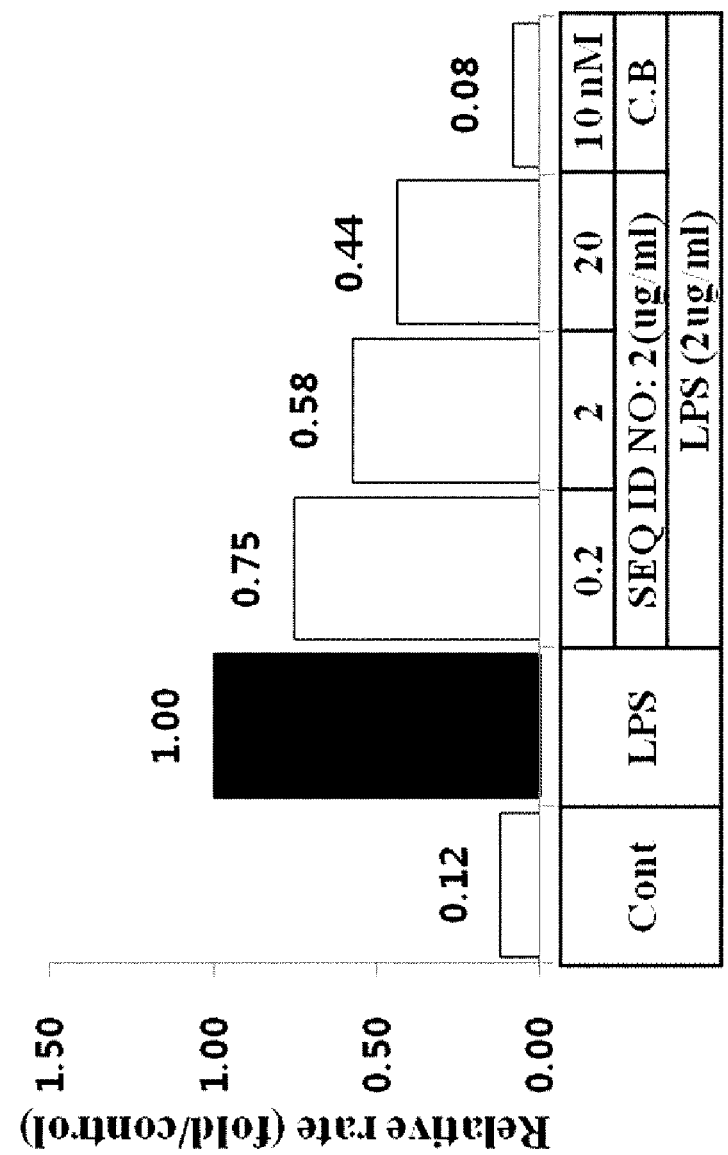
FIG. 2d is a graph of the western blot results confirming the expression change of COX2 by a peptide composed of the amino acid sequence of SEQ ID NO: 2 according to an embodiment of the present invention.
Figure 2E:
FIG. 2e shows the western blot results confirming the expression change of COX2 by a peptide composed of the amino acid sequence of SEQ ID NO: 3 according to an embodiment of the present invention.
Figure 2F:
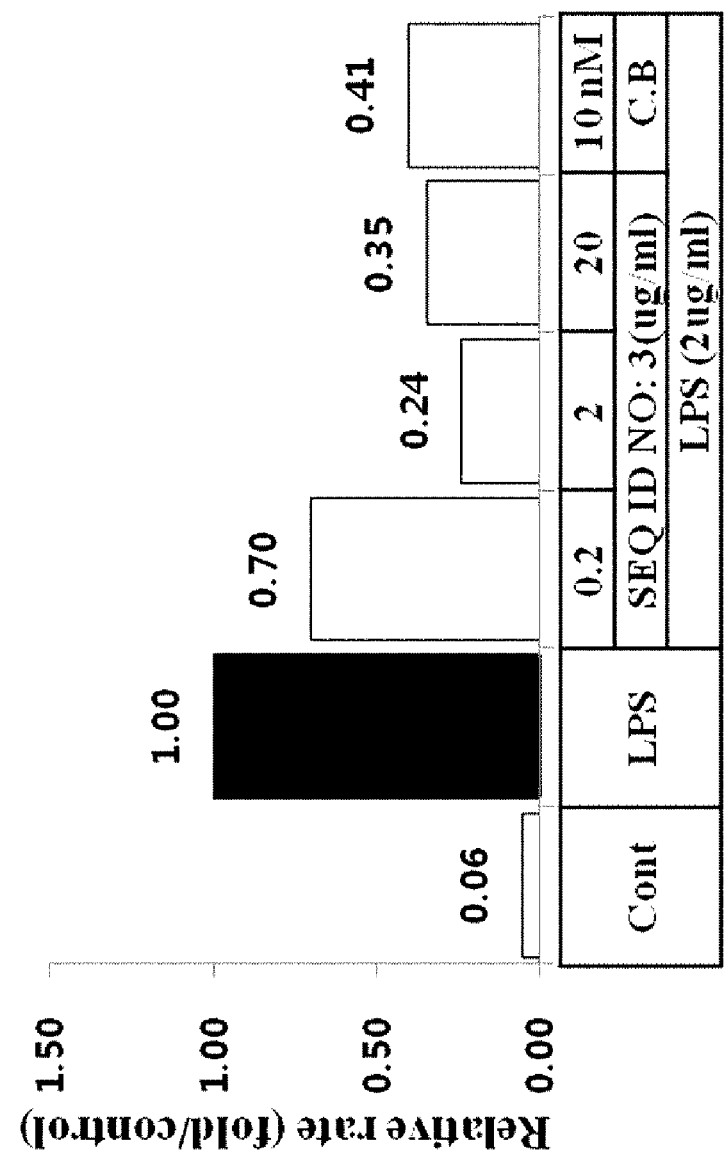
FIG. 2f is a graph of the western blot results confirming the expression change of COX2 by a peptide composed of the amino acid sequence of SEQ ID NO: 3 according to an embodiment of the present invention.

The present invention relates to a peptide having anti-inflammatory activity and consisting of an amino acid sequence of SEQ ID NO: 1, SEQ ID NO: 2 or SEQ ID NO: 3.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Synthesis Example 1: Peptide Synthesis 700 mg of chlorotrityl chloride resin (CTL resin, Nova Biochem Cat No. 01-64-0021) was placed in a reaction container, and 10 ml of methylene chloride (MC) was added, followed by stirring for 3 minutes.

After the solution was removed, 10 ml of dimethyl form amide (DMF) was added, followed by stirring for 3 minutes, and then the solvent was again removed. After 10 ml of a dichloromethane solution was placed in the reactor, and 200 mmole Fmoc-Asp(OtBu)-OH (Bachem, Swiss) and 400 mmole diisopropyl ethylamine (DIEA) were added thereto, the mixture was well dissolved with stirring, followed by reaction with stirring for 1 hour.

After the reaction, washing was conducted, and then methanol and DIEA (2:1) were dissolved in dichloromethane (DCM) to conduct reaction for 10 minutes, followed by washing with excessive DCM/DMF (1:1).

After the solution was removed, 10 ml of dimethyl form amide (DMF) was added, followed by stirring for 3 minutes, and then the solvent was again removed. 10 ml of a deprotection solution (20% piperidine/DMF) was placed in the reaction container, followed by stirring at room temperature for 10 minutes, and then the solution was removed. An equal amount of a deprotection solution was added, and then the reaction was again maintained for 10 minutes, and thereafter, the solution was removed, followed by washing twice with DMF, once with MC, and once with DMF, for 3 minutes each, thereby preparing Asp(OtBu)-CTL Resin.

10 ml of a DMF solution was placed in a new reactor, and 200 mmol Fmoc-Arg(Pbf)-OH (Bachem, Swiss), 200 mmol HoBt, and 200 mmole Bop were added, and the mixture was well dissolved with stirring.

After 400 mmole DIEA was added to the reactor in two divided portions, stirring was conducted for at least 5 minutes until all solids were dissolved. The dissolved amino acid mixed solution was added to the reaction container containing the deprotected resin therein, and the reaction was conducted with stirring at room temperature for 1 hour. After the reaction liquid was removed, stirring was conducted using a DMF solution three times for 5 minutes each, followed by removal. A small amount of the reaction resin was taken to check the extent of reaction using the Kaiser test (Ninhydrin test).

The deprotection reaction was twice conducted using a deprotection solution in the same manner as described above, thereby preparing Arg(Pbf)-Asp(OtBu)-CTL Resin. After sufficient washing with DMF and MC, the Kaiser test was again conducted, and then the following amino acid attachment test was conducted in the same manner as described above.

A chain reaction was conducted in the order of Fmoc-Met-OH and Fmoc-Thr (tBu)-OH according to the selected amino acid sequence. The Fmoc-protecting group was removed by reaction twice with the deprotection solution for 10 minutes for each and then well washed. After acetic anhydride, DIEA, and HoBt were added to conduct acetylation for 1 hour, the prepared peptidyl resin was washed with DMF, MC, and methanol three times each, dried under the slow flow of nitrogen gas, and completely dried by vacuum decompression under P2O5. Thereafter, 30 ml of a leaving solution [95% trifluoroacetic acid (TFA), 2.5% distilled water, and 2.5% thioanisole] was added, and the reaction was maintained for 2 hours while the mixture was intermittently stirred at room temperature.

The resin was obtained through filtration, washed with a small amount of a TFA solution, and then mixed with the stock solution.

After distillation was conducted under reduced pressure to reduce the total volume by half, 50 ml of cold ether was added to induce precipitation, and then the precipitates were collected by centrifugation, followed by washing twice with cold ether.

The stock solution was removed, followed by sufficient drying under nitrogen, thereby synthesizing 0.8 g of a peptide including the amino acid sequence of SEQ ID NO: 1 before purification (yield: 90.1%).

The molecular weight thereof was determined as 521.6 (theoretical value: 521.5) by using a molecular weight analysis system.

A peptide consisting of the amino acid sequence of SEQ ID NO: 2 or SEQ ID NO: 2 was synthesized by the method as described above.

TABLE 1

| SEQ ID NO | Amino acid sequence | Analysis value (Mass spectrometer) | |
|---|---|---|---|
| | | Analytic value | Theoretical value |
| 1 | Thr-Met-Arg-Asp | 521.6 | 521.5 |
| 2 | Asp-Asn-Cys-Leu-Arg | 619.7 | 619.6 |
| 3 | Gly-Val-Gln-His-Gln-Ala-Ser-Pro-Tyr | 986.0 | 986.0 |

Example 1: TNF-α & IL-2 RT-PCR

After 6-7-week-old mice were sacrificed to obtain spleen, the spleen was crushed using a cell filter, and centrifuged with serum-free RPMI 1640 medium. The upper layer was discarded, and for removal of red blood cells (RBC), RBC lysis buffer was used.

RBC was removed twice, followed by washing with serum-free RPMI1640 medium, and then an appropriate amount of serum-free RPMI1640 medium was added.

The cells were counted, and seeded in 96-well plate ($1\times10^6$ cells/well) and 24-well plate ($1\times10^7$ cells/dish). The next day, the cells were treated with respective peptide samples (0.2, 2, 20 ug/ml) and the stimulator LPS. Here, the experiment was performed by adjusting the time point.

Total RNA was extracted using Easy Blue (Intron). For synthesis of single-stranded DNA from RNA, RT premix (Intron) was used, and 3 ug of RNA, 2 ug of random hexamer, and DEPC-treated water were added thereto to reach a total volume of 20 ul, followed by reaction for 5 minutes at 65° C. and 1 hour at 42° C. Heating was again conducted at 95° C. for 5 minutes to prepare cDNA.

PCR was conducted by mixing 3 ul of cDNA and 10 pmole primers specific to CGI 58 gene with PCR premix (Intron). PCR conditions were: 94° C. for 30 seconds, 55-56° C. for 30 seconds, and 72° C. for 30 seconds. Genes were analyzed in the conditions in which the PCR results could be exponentially amplified. 5 ul of PCR product was obtained, electrophoresed on 1% agarose gel, and stained with ethidium bromide. The results are shown in FIGS. 1a to 1i.

TABLE 2

| SEQ ID NO | Primer name | Sequence (5'-3') |
|---|---|---|
| 4 | TNF-α Forward | CGTCAGCCGATTRTGCTATCT |
| 5 | TNF-α Reward | CGGACTCCGCAAAGTCTAAG |
| 6 | IL-2 Forward | CTCGCTTCCTGTGTCACATT |
| 7 | IL-2 Reward | ATCCTGGGGAGTTTCAGGTT |

As can be confirmed from FIGS. 1a to 1i, the expression of TNF-α and IL-2 was observed to tend to decrease in the treatment with the peptide including the amino acid sequence of SEQ ID NO: 1, SEQ ID NO: 2 or SEQ ID NO: 3.

Example 2: Western Blot

The splenocytes obtained in example 1 were seeded in 24-well plate at cell density of $1\times10^7$ cells/well. Then, after incubation overnight, the cells were treated with the peptides of SEQ ID NO: 1, SEQ ID NO: 2 and SEQ ID NO: 3 with different concentrations (0.2-20 ug/ml), followed by incubation in an incubator at 37° C. for 24 hours, and then the cells were treated with cell lysis buffer to secure lysate, followed by protein quantification. Then, western blotting with respect to the inflammation inducing factor COX2 was conducted, and the results are shown in FIGS. 2a to 2f.

As can be confirmed from FIGS. 2a to 2f, the expression of COX2 was reduced when treated with the peptide including the amino acid sequence of SEQ ID NO: 1, SEQ ID NO: 2 or SEQ ID NO: 3.

Example 3: ELISA 3-1: ELISA (Splenocytes)

The splenocytes treated with the peptide samples and the stimulator LPS in example 1 were incubated for 48 hours, and then the culture media were collected. The obtained media were subjected to an experiment using an ELISA kit (R&D system) for cytokines (TNF-α and INF-γ) to be investigated.

3-2: ELISA (Raw264.7 Cells)

Raw264.7 cells were seeded at $1\times10^6$ cells/48-well, and incubated overnight. The cells were pre-treated with samples to be investigated at 0.2, 2, and 20 ug/ml, and after 30 minutes, the cells were treated with LPS. Incubation was conducted at the scheduled time point. After 24 hours, the culture media were collected, and the obtained media were subjected to an experiment using an ELISA kit (R&D system) for cytokine (TNF-α) to be investigated.

As can be confirmed from FIGS. 3a to 3d, the secretion of TNF-α and INF-γ was decreased in the splenocytes and the secretion of TNF-α tended to decrease in RAW264.7 cells in the treatment with the peptide including the amino acid sequence of SEQ ID NO: 1 or SEQ ID NO: 2.

Figure 3A:
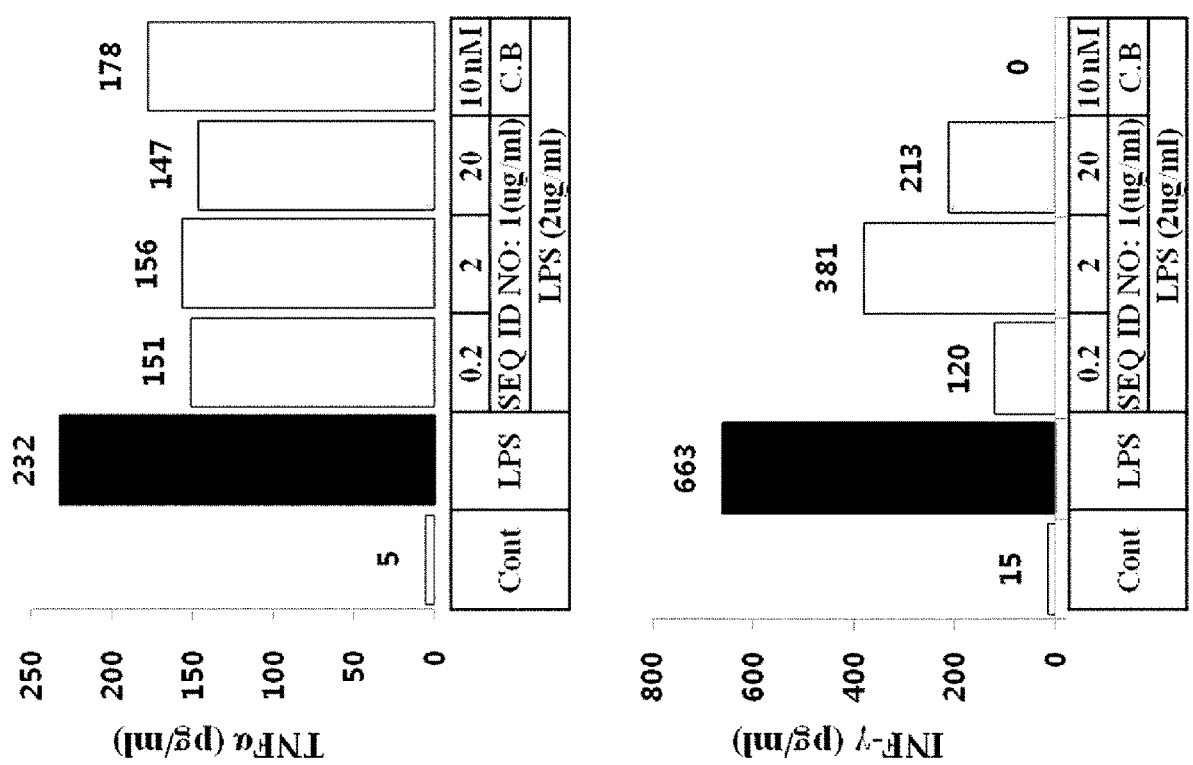
FIG. 3a shows the ELISA results confirming the secretion changes of TNF-α and INF-γ in splenocytes by a peptide composed of the amino acid sequence of SEQ ID NO: 1 according to an embodiment of the present invention.
Figure 3B:
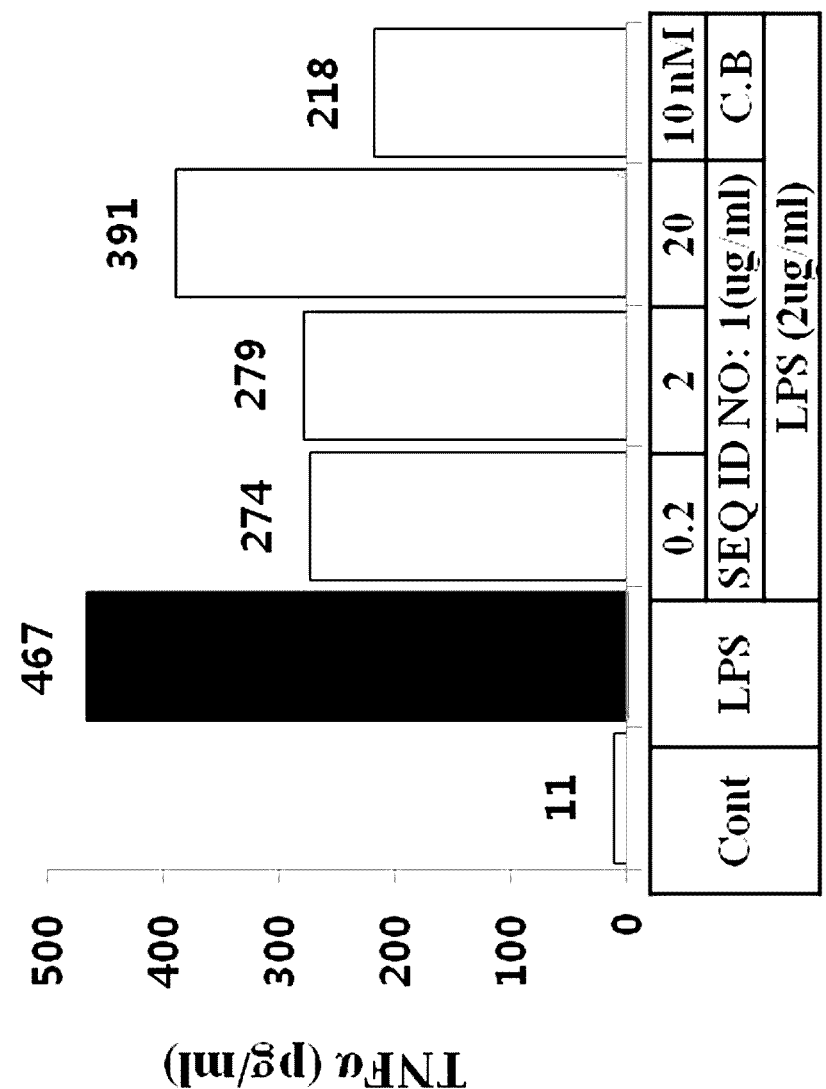
FIG. 3b shows the ELISA results confirming the secretion change of TNF-α in macrophages by a peptide composed of the amino acid sequence of SEQ ID NO: 1 according to an embodiment of the present invention.
Figure 3C:
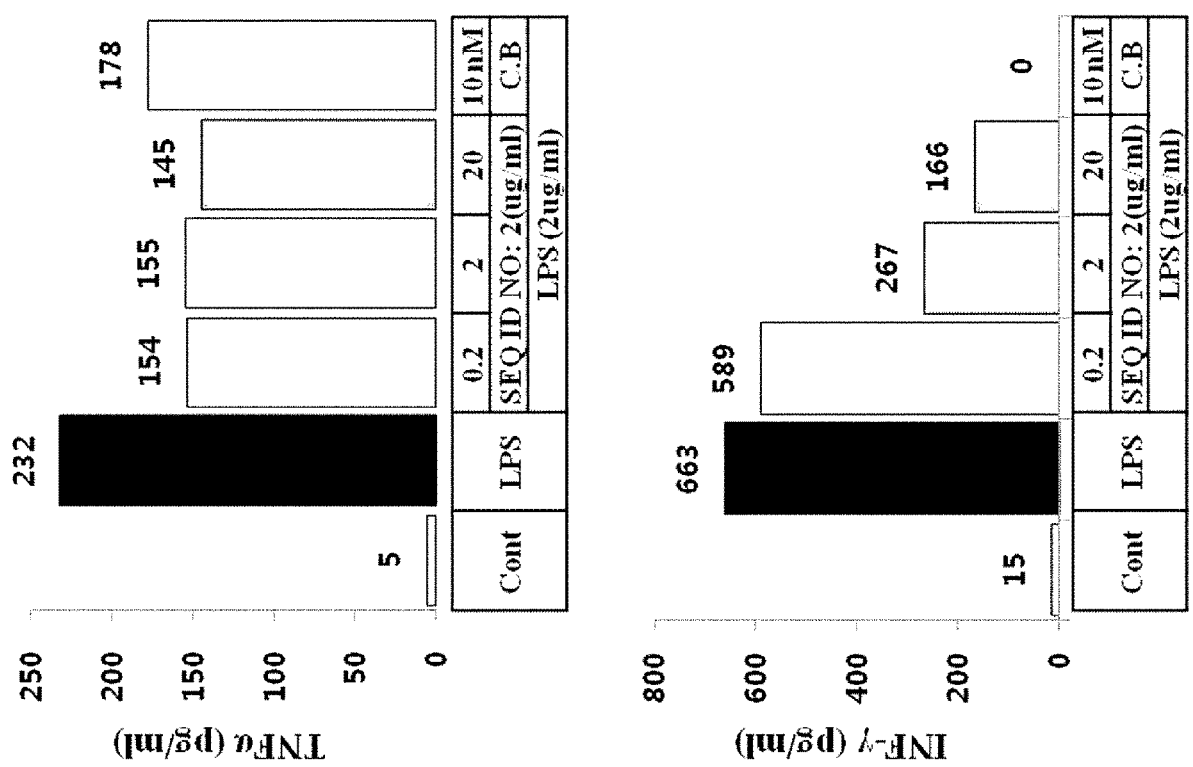
FIG. 3c shows the ELISA results confirming the secretion changes of TNF-α and INF-γ in splenocytes by a peptide composed of the amino acid sequence of SEQ ID NO: 2 according to an embodiment of the present invention.
Figure 3D:
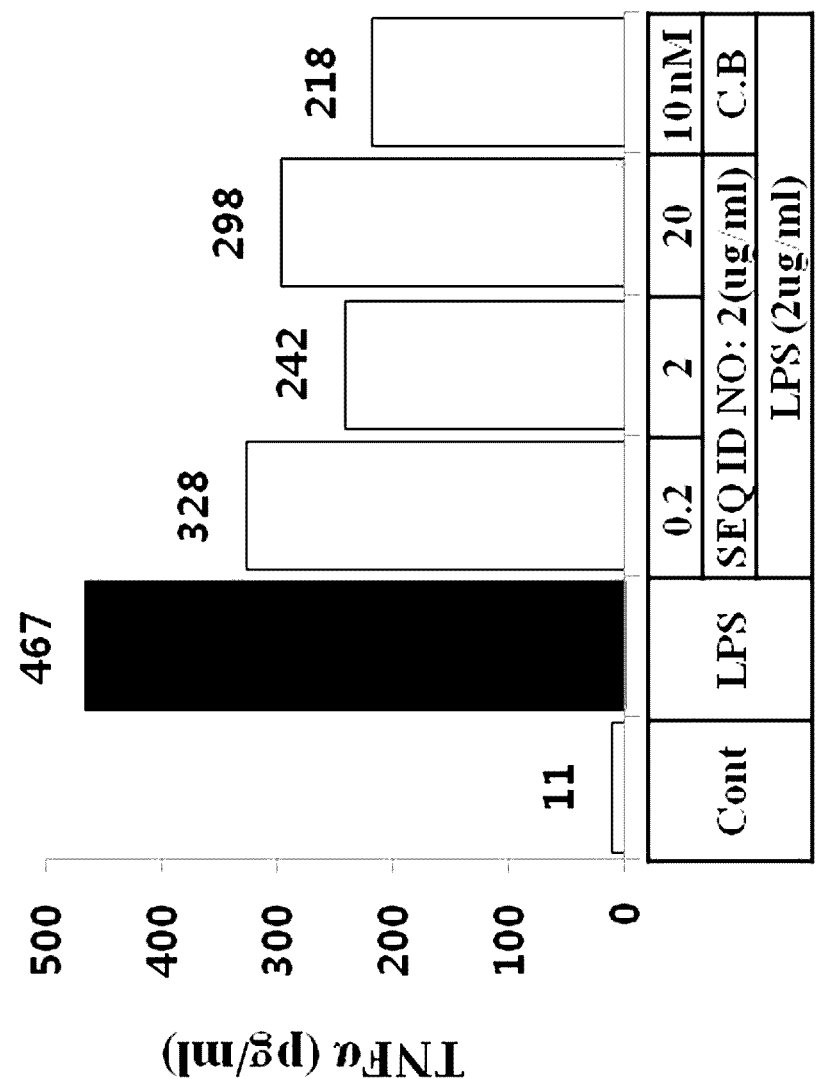
FIG. 3d shows the ELISA results confirming the secretion change of TNF-α in macrophages by a peptide composed of the amino acid sequence of SEQ ID NO: 2 according to an embodiment of the present invention.
Figure 3E:
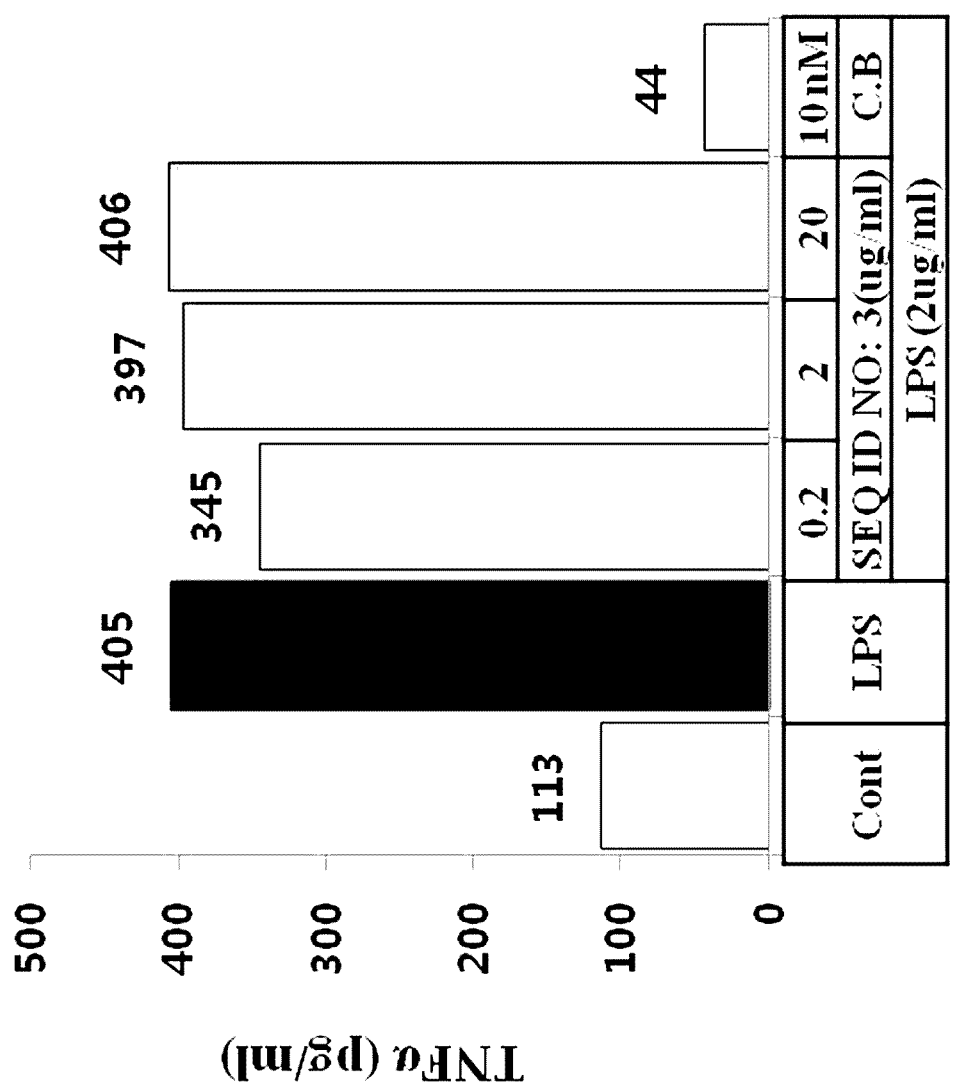
FIG. 3e shows the ELISA results confirming the secretion change of TNF-α in macrophages by a peptide composed of the amino acid sequence of SEQ ID NO: 3 according to an embodiment of the present invention.
Figure 4A:
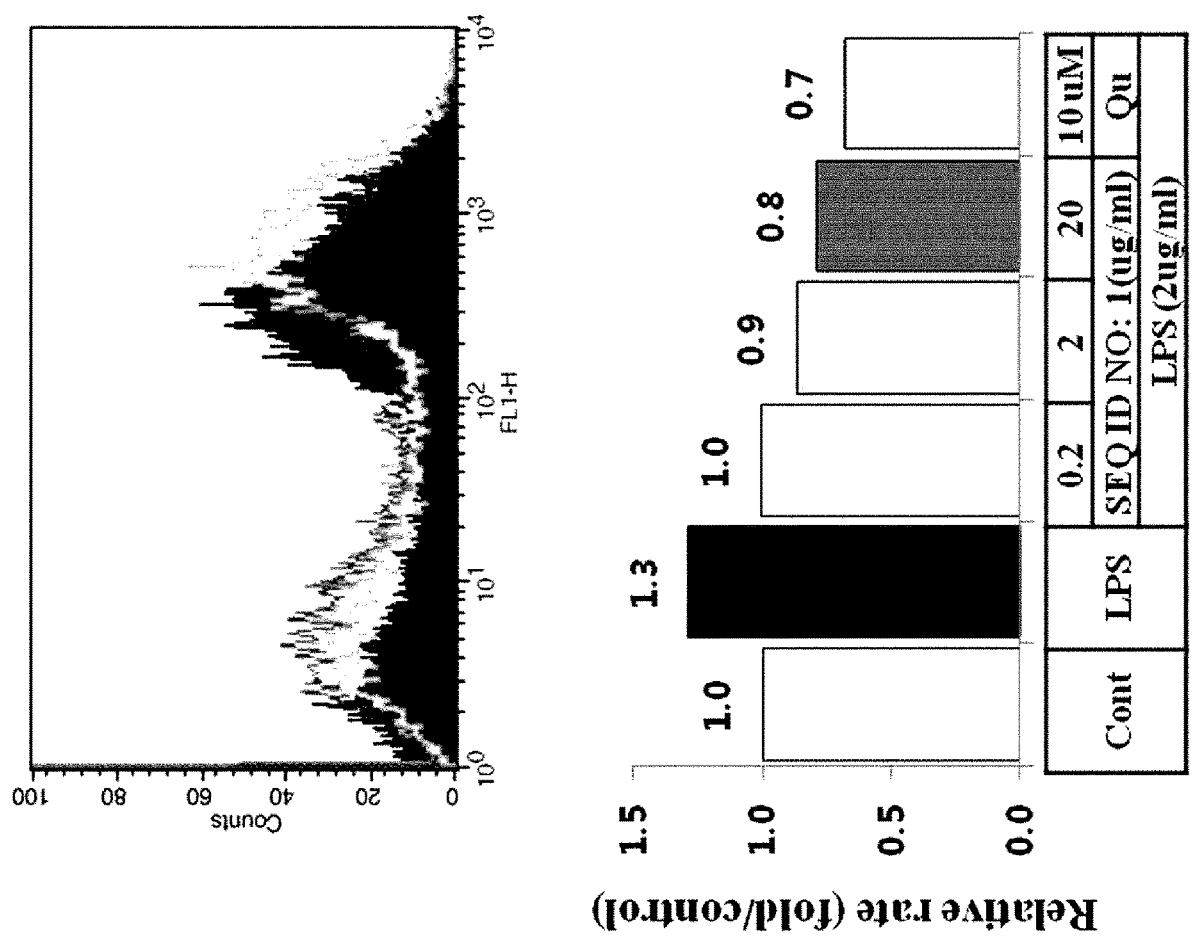
FIG. 4a shows the measurement results of the reduction of ROS production by a peptide composed of the amino acid sequences of SEQ ID NO: 1 according to an embodiment of the present invention.
Figure 4B:
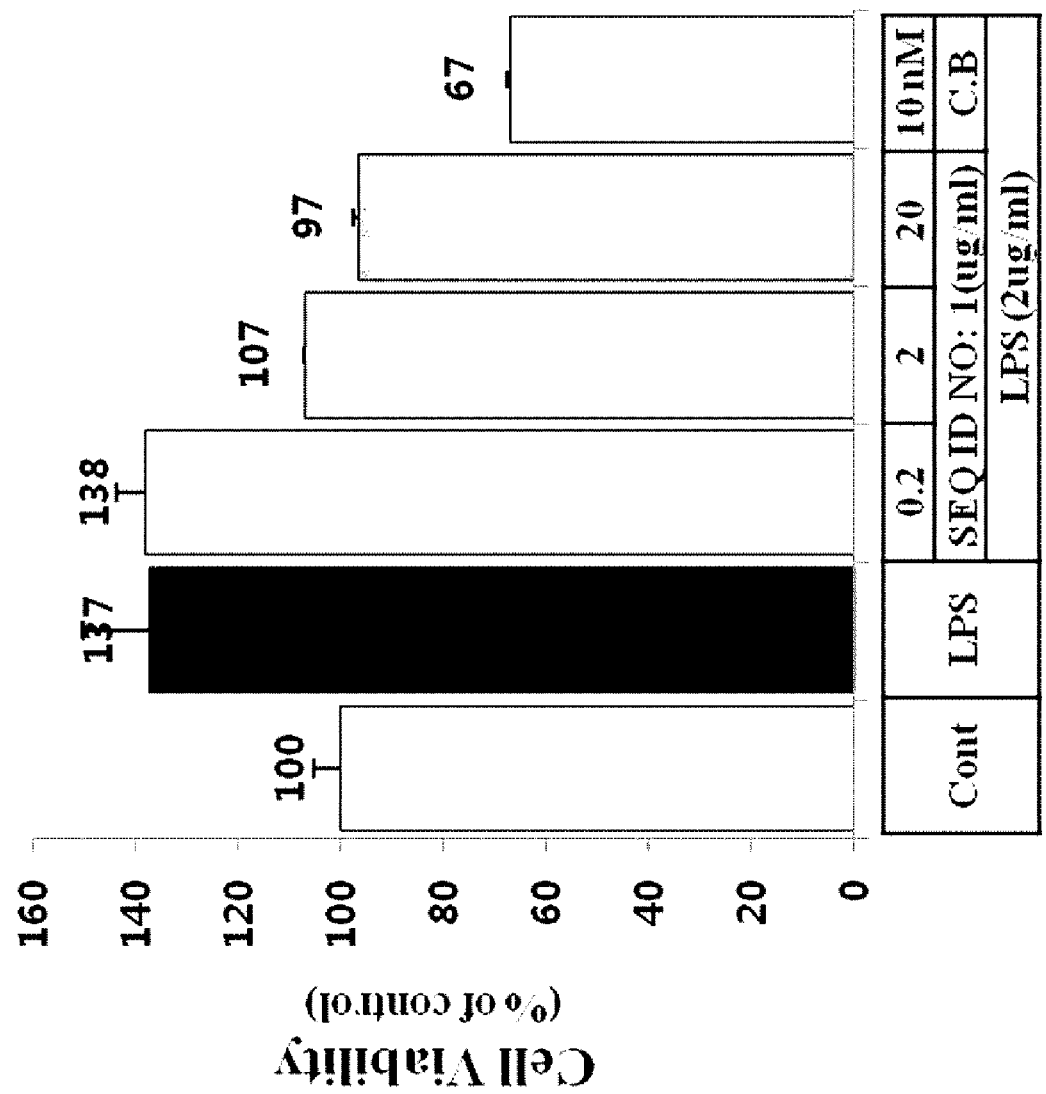
FIG. 4b shows the proliferation assay results by a peptide composed of the amino acid sequence of SEQ ID NO: 1 according to an embodiment of the present invention.
Figure 4C:
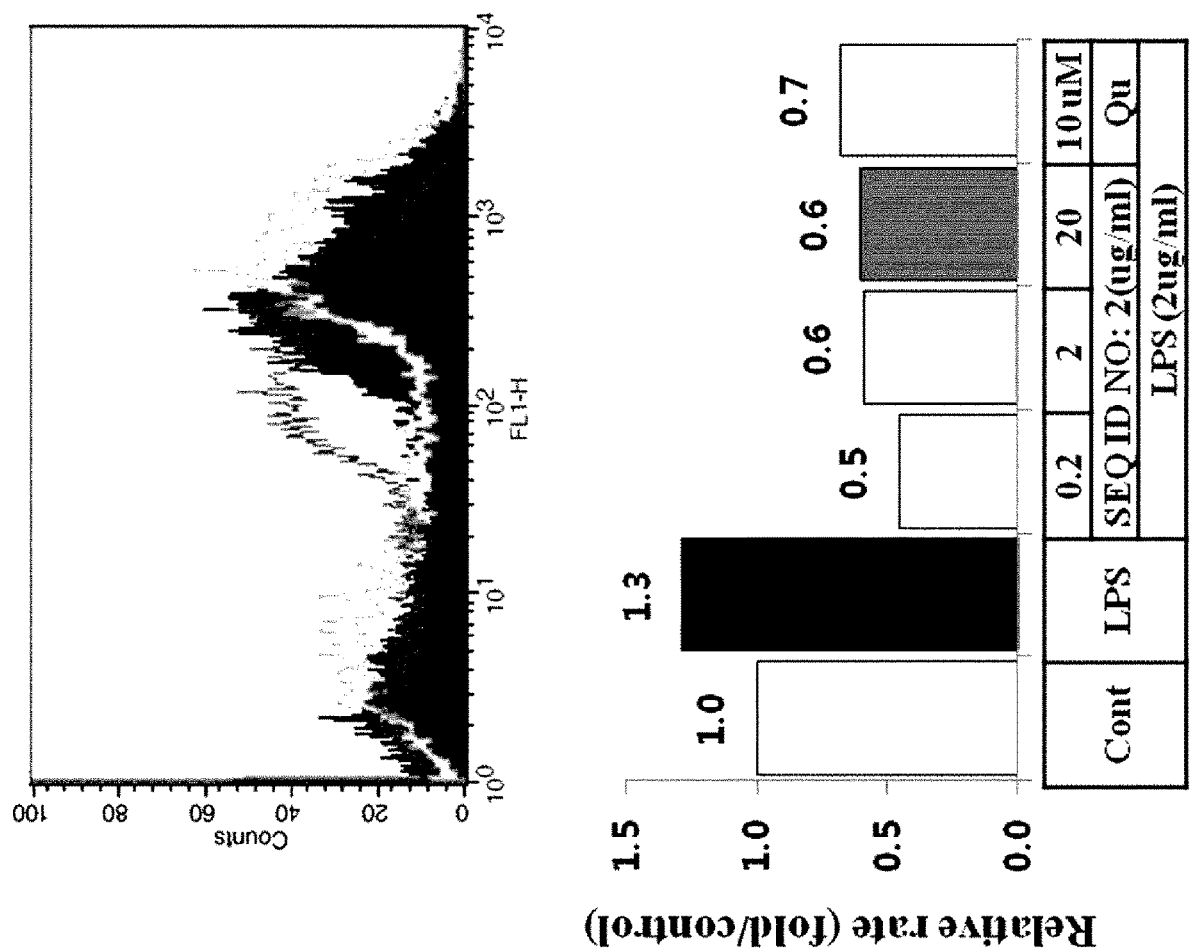
FIG. 4c shows the measurement results of the reduction of ROS production by a peptide composed of the amino acid sequences of SEQ ID NO: 2 according to an embodiment of the present invention.
Figure 4D:
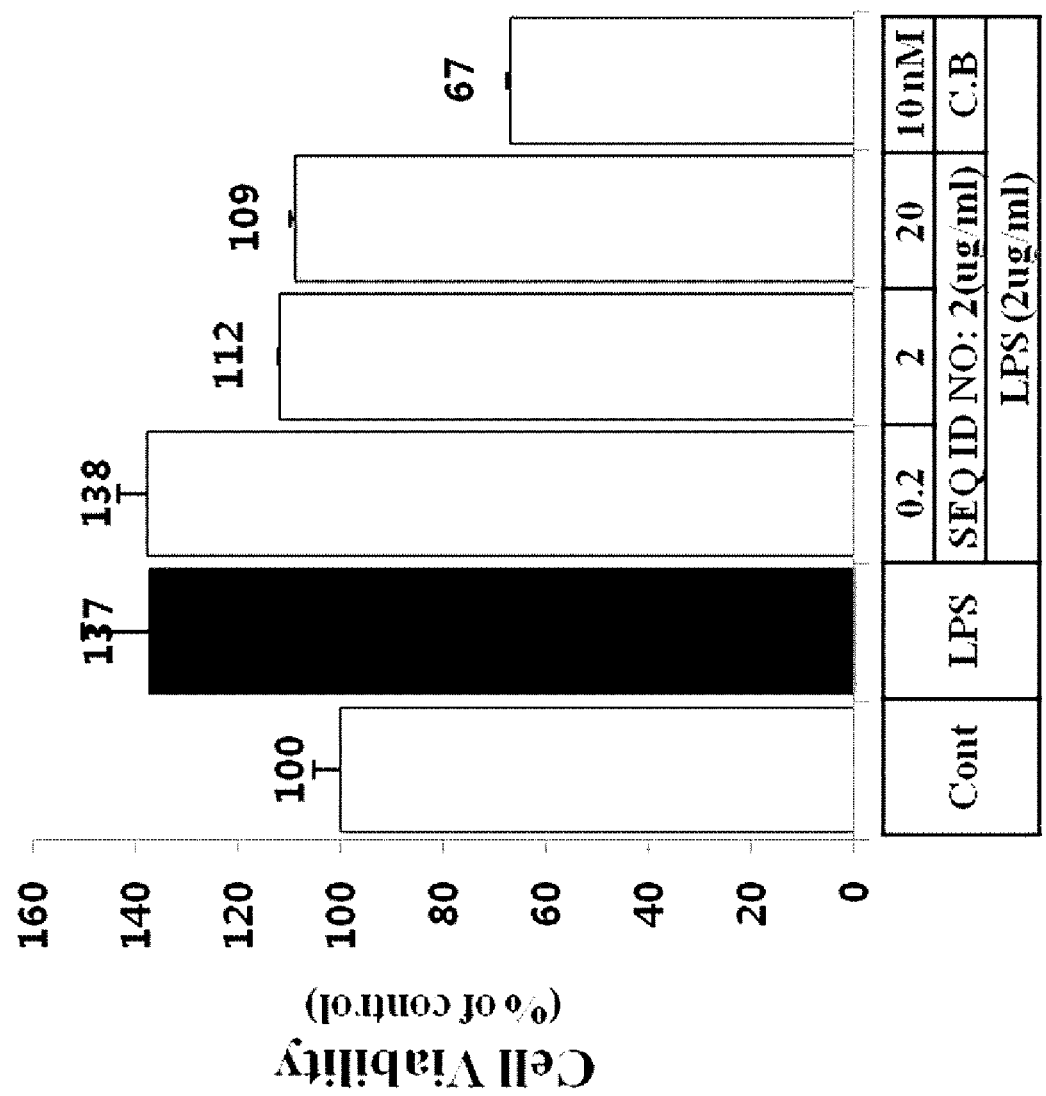
FIG. 4d shows the proliferation assay results by a peptide composed of the amino acid sequence of SEQ ID NO: 2 according to an embodiment of the present invention.
Figure 4E:
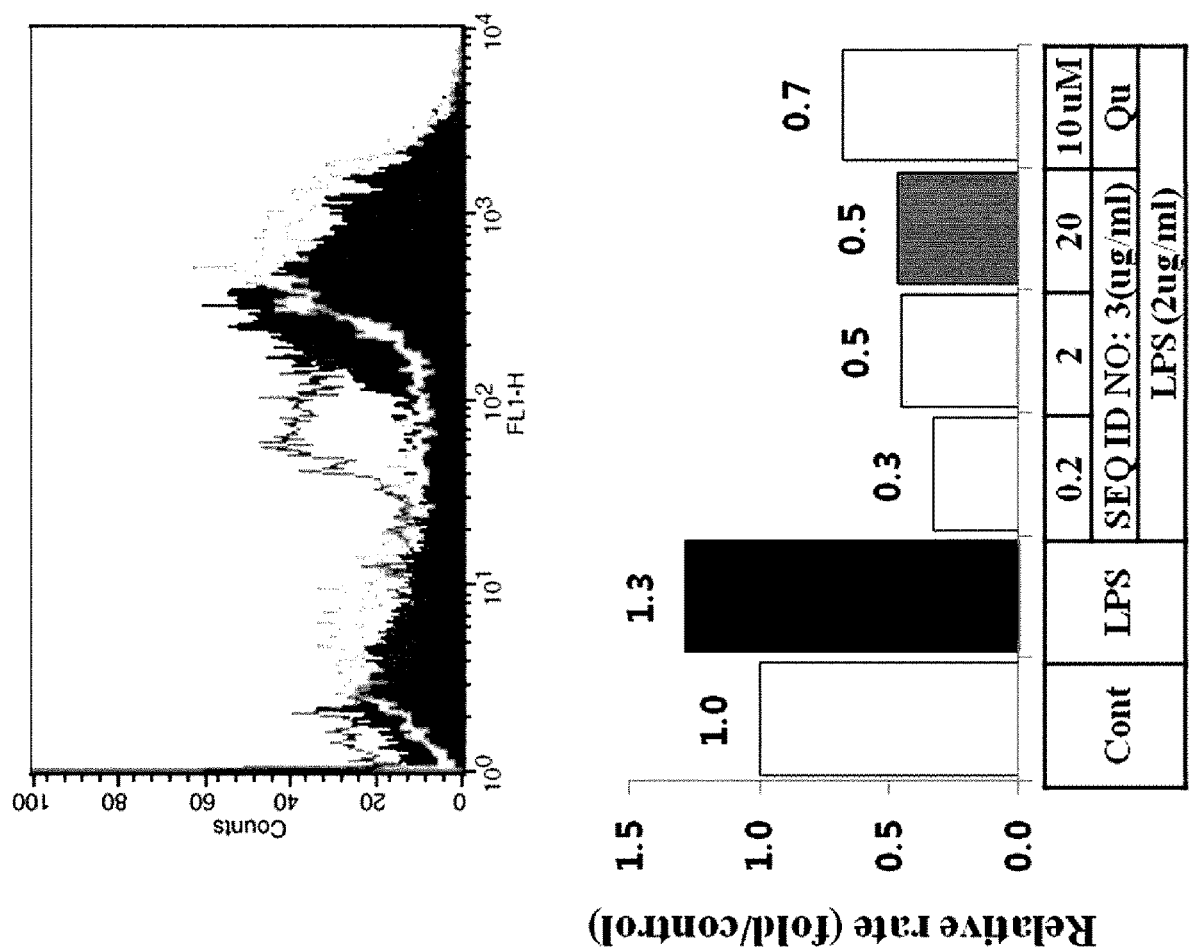
FIG. 4e shows the measurement results of the reduction of ROS production by a peptide composed of the amino acid sequences of SEQ ID NO: 3 according to an embodiment of the present invention.
Figure 5A:
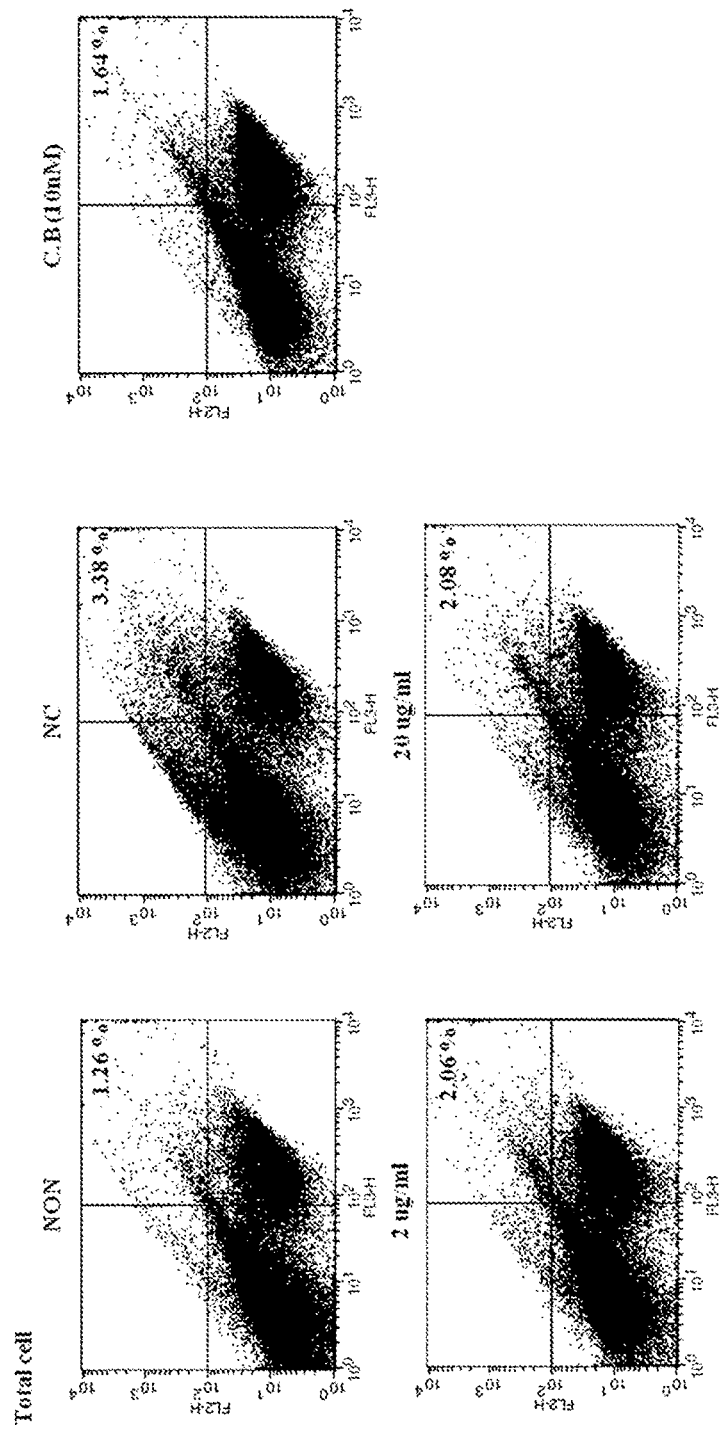
FIG. 5a shows the results of FACS analysis of CD3+ and CD25+ when splenocytes were treated with a peptide composed of the amino acid sequence of SEQ ID NO: 1 according to an embodiment of the present invention.
Figure 5B:
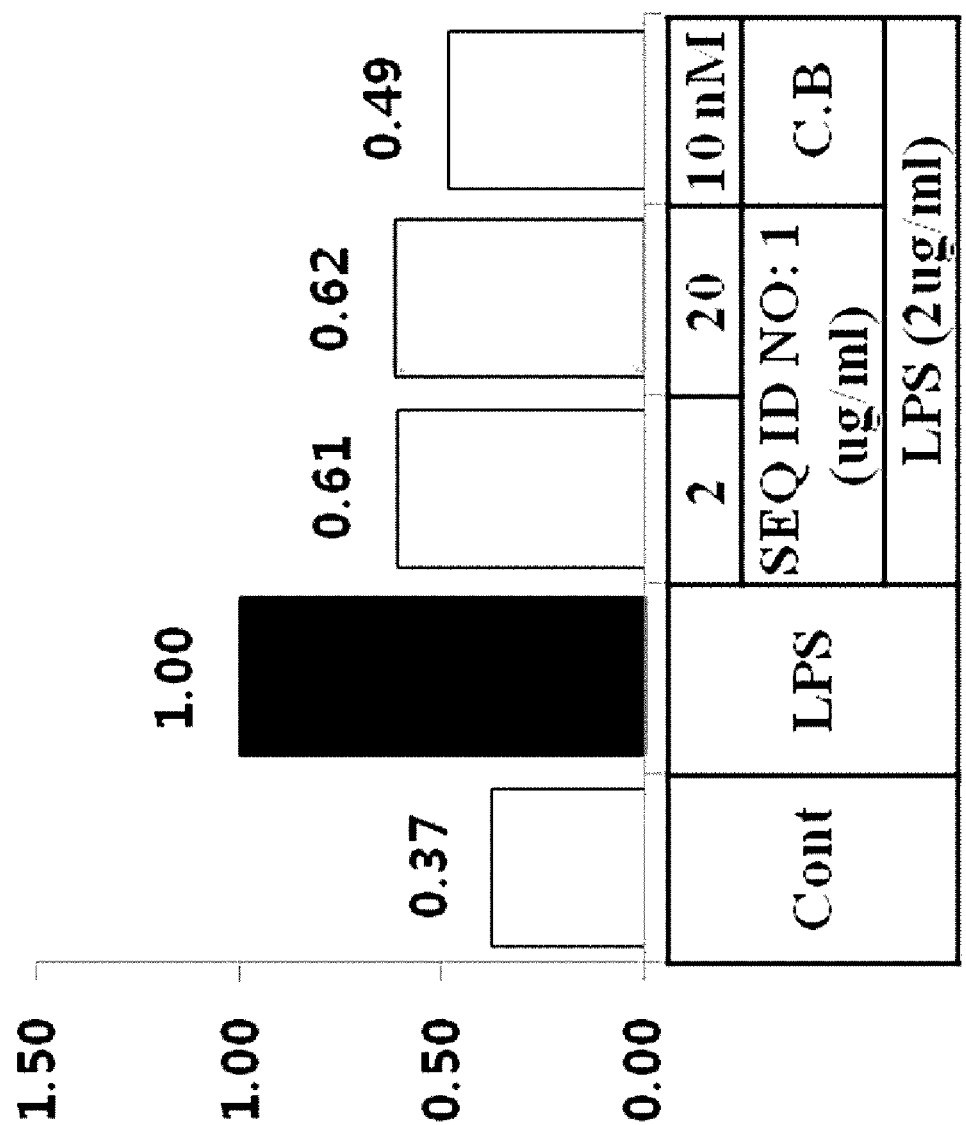
FIG. 5b is a graph of FACS analysis of CD3+ and CD25+ when splenocytes were treated with a peptide composed of the amino acid sequence of SEQ ID NO: 1 according to an embodiment of the present invention.
Figure 5C:
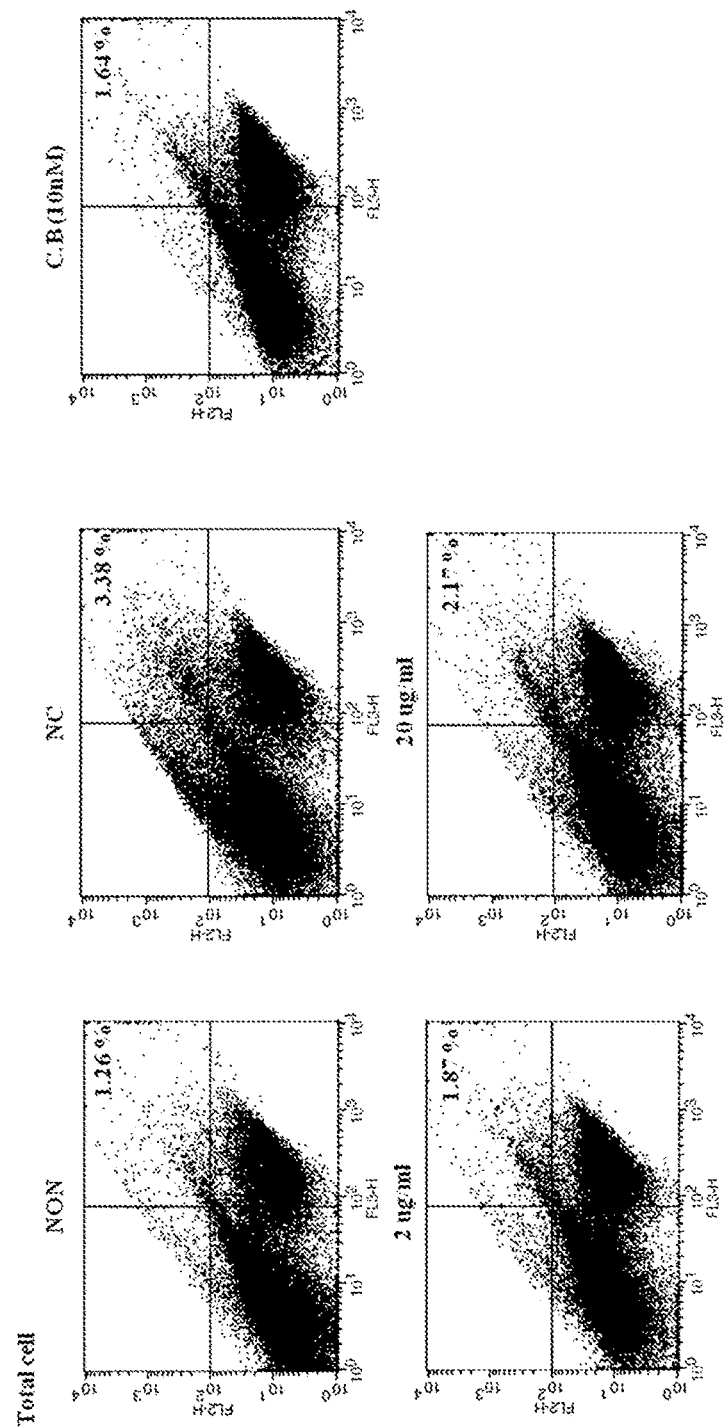
FIG. 5c shows the results of FACS analysis of CD3+ and CD25+ when splenocytes were treated with a peptide composed of the amino acid sequence of SEQ ID NO: 2 according to an embodiment of the present invention.
Figure 5D:
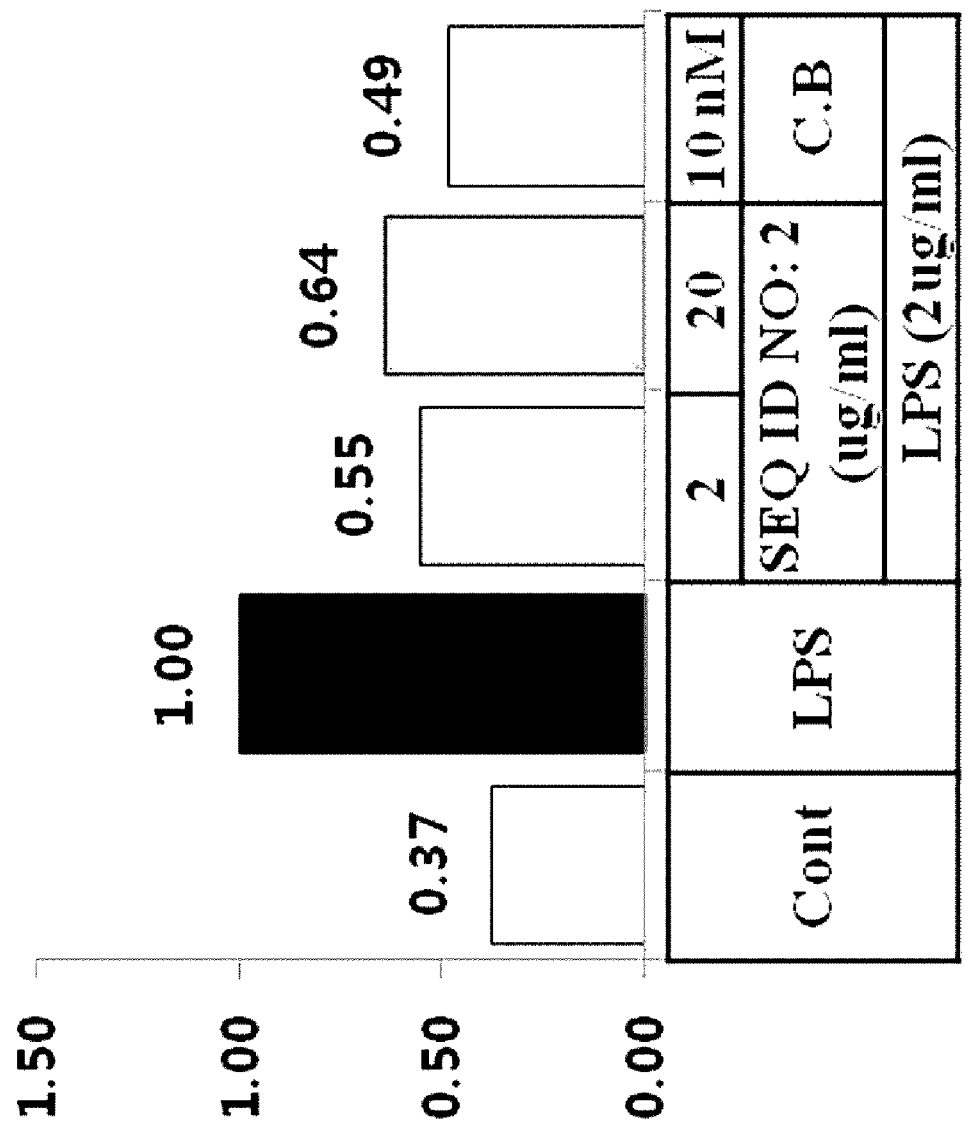
FIG. 5d is a graph of FACS analysis of CD3+ and CD25+ when splenocytes were treated with a peptide composed of the amino acid sequence of SEQ ID NO: 2 according to an embodiment of the present invention.
Figure 5E:
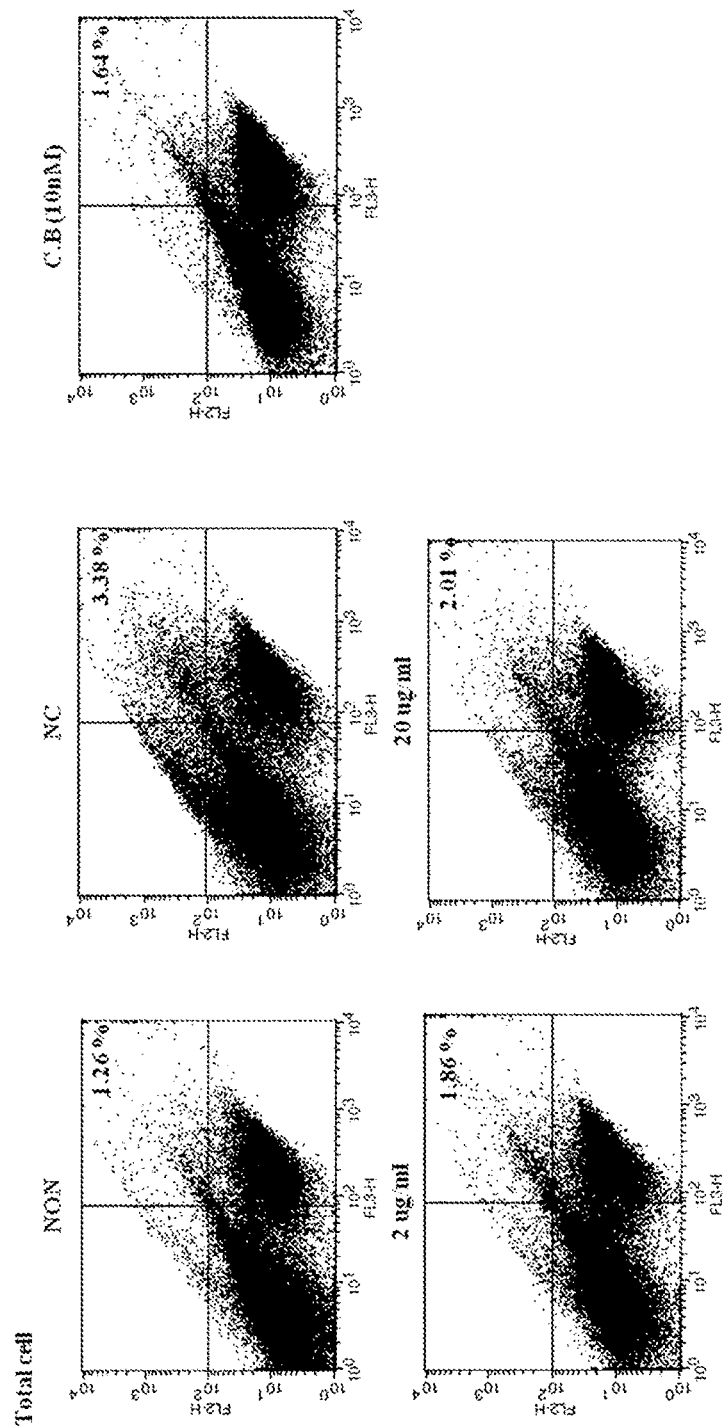
FIG. 5e shows the results of FACS analysis of CD3+ and CD25+ when splenocytes were treated with a peptide composed of the amino acid sequence of SEQ ID NO: 3 according to an embodiment of the present invention.
Figure 5F:
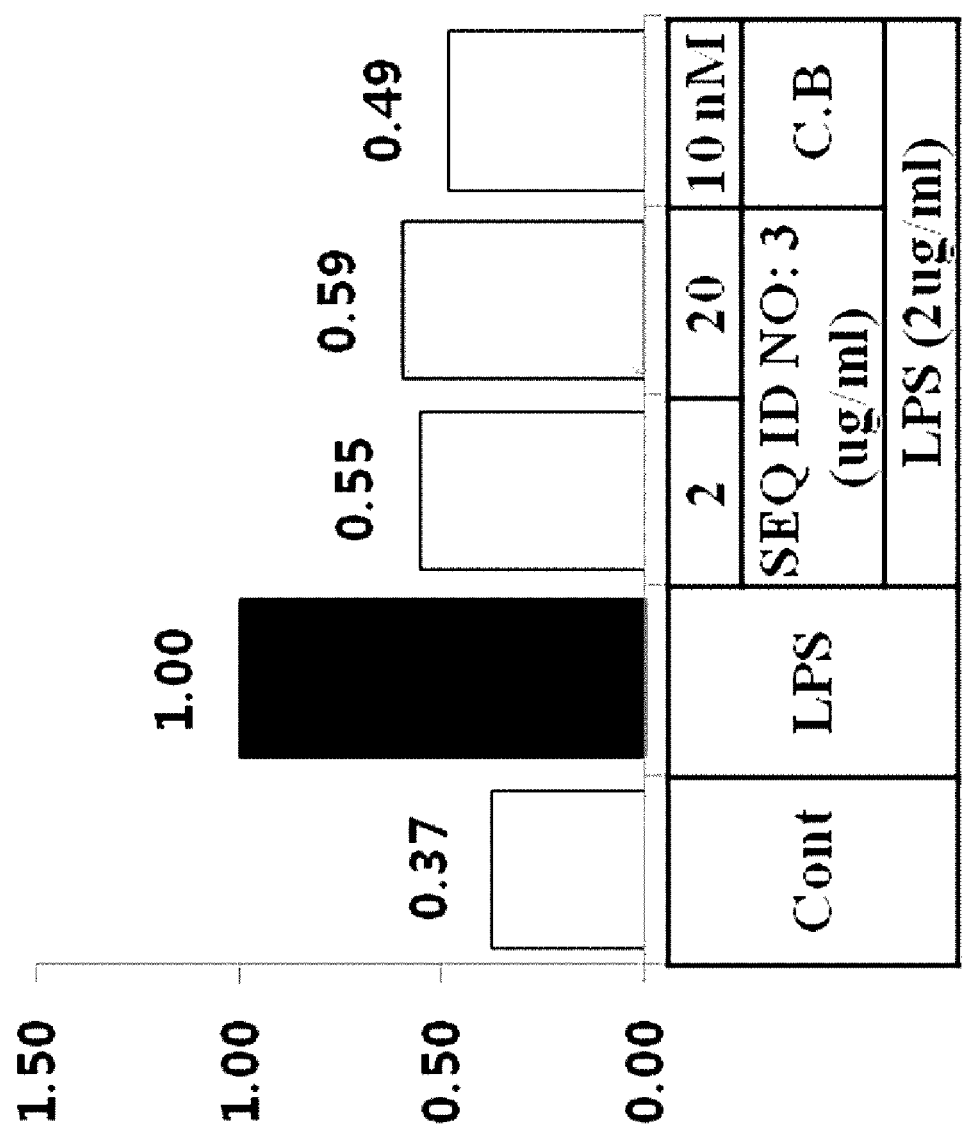
FIG. 5f is a graph of FACS analysis of CD3+ and CD25+ when splenocytes were treated with a peptide composed of the amino acid sequence of SEQ ID NO: 3 according to an embodiment of the present invention.

As can also be confirmed from FIG. 3e, the secretion of TNF-α was decreased in RAW264.7 cells in the treatment with the peptide including the amino acid sequence of SEQ ID NO: 3.

Example 4: Proliferation Assay and FACS 4-1. Proliferation Assay (Splenocytes)

As described in example 1, the experiment was conducted using Ez-cytox kit 24 hours after the treatment with the peptide sample and the stimulator LPS.

4-2. FACS [Intracellular ROS Assay (DCF-DA)]

Raw264.7 cells were seeded at $1\times10^6$ cells/6-well, and incubated overnight. The cells were pre-treated with samples to be investigated at 1, 10, and 50 ug/ml, and after 30 minutes, the cells were treated with LPS. The cells were incubated according to the scheduled time point, and then 30 minutes after the treatment with DCF-DH, the oxidation activity was measured by the degree of fluorescence using FACS. The results are shown in FIGS. 4a to 4f.

As can be confirmed from FIGS. 4a to 4f, the ROS production was reduced when treated with the peptide including the amino acid sequence of SEQ ID NO: 1, SEQ ID NO: 2, or SEQ ID NO: 3. The splenocyte viability was reduced when treated with the peptides in the proliferation assay.

Example 5: Activation T Cell Analysis (FACS System)

The cells were treated with the peptide samples and the stimulator LPS as described in example 1, and after 24 hours, the cells were treated with antibody (CD3 and CD25) activation T cell markers for 30 minutes, followed by washing twice with PBS, and then FACS was conducted. The results are shown in FIGS. 5a to 5f.

As can be confirmed from FIGS. 5a to 5f, the CD3+ and CD25+ cells were decreased when treated with the peptide including the amino acid sequence of SEQ ID NO: 1, SEQ ID NO: 2, or SEQ ID NO: 3.

INDUSTRIAL APPLICABILITY

The present invention relates to a peptide having anti-inflammatory activity and a use thereof.

---

The invention claimed is:

1. A peptide having anti-inflammatory activity, the peptide consisting of the amino acid sequence of SEQ ID NO: 1, SEQ ID NO: 2 or SEQ ID NO: 3, optionally wherein the peptide has a protecting group linked to the N- or C-terminus of the peptide.

2. The peptide of claim 1, wherein the peptide inhibits the expression of an inflammatory cytokine.

3. The peptide of claim 1, wherein the inflammatory cytokine is at least one selected from the group consisting of TNF-α (tumor necrosis factor-α), IL-2 and INF-γ.

4. The peptide of claim 1, wherein the peptide inhibits the expression of cycooxygenase-2 (COX-2).

5. The peptide of claim 1, wherein the peptide reduces ROS production.

6. The peptide of claim 1, wherein the peptide suppresses the proliferation of inflammatory cells.

7. The peptide of claim 1, wherein the peptide suppresses the activation of T cells.

8. The peptide of claim 1, wherein the protecting group is selected from the group consisting of an acetyl group, a fluorenyl methoxy carbonyl group, a formyl group, a palmitoyl group, a myristyl group, a stearyl group, and polyethylene glycol (PEG).

9. The peptide of claim 1, wherein the peptide consists of the sequence of SEQ ID NO: 1.

10. The peptide of claim 1, wherein the peptide consists of the sequence of SEQ ID NO: 2.

11. The peptide of claim 1, wherein the peptide consists of the sequence of SEQ ID NO: 3.

12. The peptide of claim 1, wherein the peptide has a protecting group linked to the N- or C-terminus of the peptide, and the protecting group is selected from the group consisting of an acetyl group, a fluorenyl methoxy carbonyl group, a formyl group, a palmitoyl group, a myristyl group, a stearyl group, and polyethylene glycol (PEG).

13. A pharmaceutical composition comprising a peptide of claim 1.

14. A method for preventing or improving an inflammatory disease comprising: administering a pharmaceutical composition comprising at least one peptide selected from the group consisting of: a peptide consisting of the amino acid sequence of SEQ ID NO: 1, a peptide consisting of the amino acid sequence of SEQ ID NO: 2, and a peptide consisting of the amino acid sequence of SEQ ID NO: 3, as an active ingredient, optionally wherein the peptide has a protecting group linked to the N- or C-terminus of the peptide.

15. The method of claim 14, wherein the inflammatory disease is any one of atopic dermatitis, encephalitis, inflammatory enteritis, chronic obstructive pulmonary disease, pulmonary hemorrhagic shock, pulmonary fibrosis, undifferentiated spondyloarthropathy, undifferentiated arthropathy, arthritis, inflammatory osteolysis, chronic inflammation diseases by chronic viral or bacterial infections, colitis, inflammatory enteropathy, type 1 diabetes, rheumatoid arthritis, reactive arthritis, osteoarthritis, psoriasis, scleroderma, osteoporosis, atherosclerosis, myocarditis, endocarditis, pericarditis, cystic fibrosis, Hashimoto's thyroiditis, Graves' disease, leprosy, syphilis, Lyme disease, borreliosis, neurogenic borreliosis, tuberculosis, sarcoidosis, lupus, discoid lupus, chilblain lupus, lupus nephritis, systemic lupus erythematosus, macular degeneration, uveitis, irritable bowel syndrome, Crohn's disease, Sjogren's syndrome, fibromyalgia, chronic fatigue syndrome, chronic fatigue and immune dysfunction syndrome, myalgic encephalomyelitis, amyotrophic lateral sclerosis, Parkinson's disease, and multiple sclerosis.

16. The method of claim 14, wherein the peptide consists of the sequence of SEQ ID NO: 1.

17. The method of claim 14, wherein the peptide consists of the sequence of SEQ ID NO: 2.

18. The method of claim 14, wherein the peptide consists of the sequence of SEQ ID NO: 3.

19. The method of claim 14, wherein the protecting group is selected from the group consisting of an acetyl group, a fluorenyl methoxy carbonyl group, a formyl group, a palmitoyl group, a myristyl group, a stearyl group, and polyethylene glycol (PEG).

20. The method of claim 14, wherein the peptide has a protecting group linked to the N- or C-terminus of the peptide, and the protecting group is selected from the group consisting of an acetyl group, a fluorenyl methoxy carbonyl group, a formyl group, a palmitoyl group, a myristyl group, a stearyl group, and polyethylene glycol (PEG).

* * * * *